(12) United States Patent
Robinson et al.

(10) Patent No.: US 12,213,745 B2
(45) Date of Patent: *Feb. 4, 2025

(54) EXTENDED REALITY SYSTEMS FOR VISUALIZING AND CONTROLLING OPERATING ROOM EQUIPMENT

(71) Applicant: GLOBUS MEDICAL, INC., Audubon, PA (US)

(72) Inventors: Michael Robinson, Concord, NH (US); Thomas Calloway, Pelham, NH (US); Isaac Dulin, Somerville, MA (US); Mir Hussain, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 525 days.

This patent is subject to a terminal disclaimer.

(21) Appl. No.: 17/476,840

(22) Filed: Sep. 16, 2021

(65) Prior Publication Data

US 2023/0083605 A1 Mar. 16, 2023

Related U.S. Application Data

(63) Continuation of application No. 17/476,689, filed on Sep. 16, 2021.

(51) Int. Cl.
*G06F 3/01* (2006.01)
*A61B 34/00* (2016.01)
(Continued)

(52) U.S. Cl.
CPC .............. *A61B 34/20* (2016.02); *A61B 34/25* (2016.02); *A61B 34/30* (2016.02); *A61B 90/361* (2016.02);
(Continued)

(58) Field of Classification Search
CPC .......... A61B 34/30; A61B 90/37; G06F 3/017
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

OTHER PUBLICATIONS

US 8,231,638 B2, 07/2012, Swarup et al. (withdrawn)

*Primary Examiner* — Samantha (Yuehan) Wang

(57) ABSTRACT

A camera tracking system receives patient reference tracking information indicating pose of a patient reference array tracked by a patient tracking camera relative to a patient reference frame. A local XR headset view pose transform is determined between a local XR headset reference frame and the patient reference frame. Remote reference tracking information is received indicating pose of a remote reference array tracked by a remote reference tracking camera. A remote XR headset view pose transform is determined between a remote XR headset reference frame of a remote XR headset and the remote reference array. A 3D computer image is transformed from a local pose determined using the local XR headset view pose transform to a remote pose determined using the remote XR headset view pose transform. The transformed 3D computer image is provided to the remote XR headset for display with the remote pose relative to the remote XR headset reference frame.

13 Claims, 14 Drawing Sheets

(51) Int. Cl.
*A61B 34/20* (2016.01)
*A61B 34/30* (2016.01)
*A61B 90/00* (2016.01)
*A61B 90/50* (2016.01)
*G06T 19/00* (2011.01)
*G06V 20/40* (2022.01)
*G06V 40/10* (2022.01)
*G06V 40/20* (2022.01)
*A61B 34/10* (2016.01)

(52) U.S. Cl.
CPC .............. *A61B 90/37* (2016.02); *A61B 90/50* (2016.02); *G06F 3/017* (2013.01); *G06T 19/00* (2013.01); *G06V 20/46* (2022.01); *G06V 40/107* (2022.01); *G06V 40/28* (2022.01); *A61B 2034/105* (2016.02); *A61B 2034/107* (2016.02); *A61B 2034/2057* (2016.02); *A61B 2034/2065* (2016.02); *A61B 2034/258* (2016.02); *A61B 2090/365* (2016.02); *A61B 2090/502* (2016.02)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |

(56) References Cited

U.S. PATENT DOCUMENTS

| | | |
|---|---|---|
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,271,132 B2 * | 9/2012 | Nielsen ................ G05D 1/0088 700/250 |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |

(56) References Cited

U.S. PATENT DOCUMENTS

| | | |
|---|---|---|
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |

(56) References Cited

U.S. PATENT DOCUMENTS

| | | |
|---|---|---|
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,916,506 B1 * | 3/2018 | Davis .................... G06V 10/22 |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |

(56) References Cited

U.S. PATENT DOCUMENTS

| | | |
|---|---|---|
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0042680 A1* | 2/2015 | Grossinger ............. G06F 3/011 345/633 |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0189568 A1* | 7/2018 | Powderly ................ G06F 3/011 |
| 2019/0005848 A1* | 1/2019 | Garcia Kilroy ........ G09B 23/28 |
| 2021/0174555 A1* | 6/2021 | Ooba ...................... G09G 5/38 |
| 2022/0151705 A1* | 5/2022 | Nikou .................. A61B 90/361 |
| 2022/0265362 A1* | 8/2022 | Marti ..................... A61B 90/37 |
| 2023/0083605 A1* | 3/2023 | Robinson ............... G06T 19/00 606/1 |

\* cited by examiner

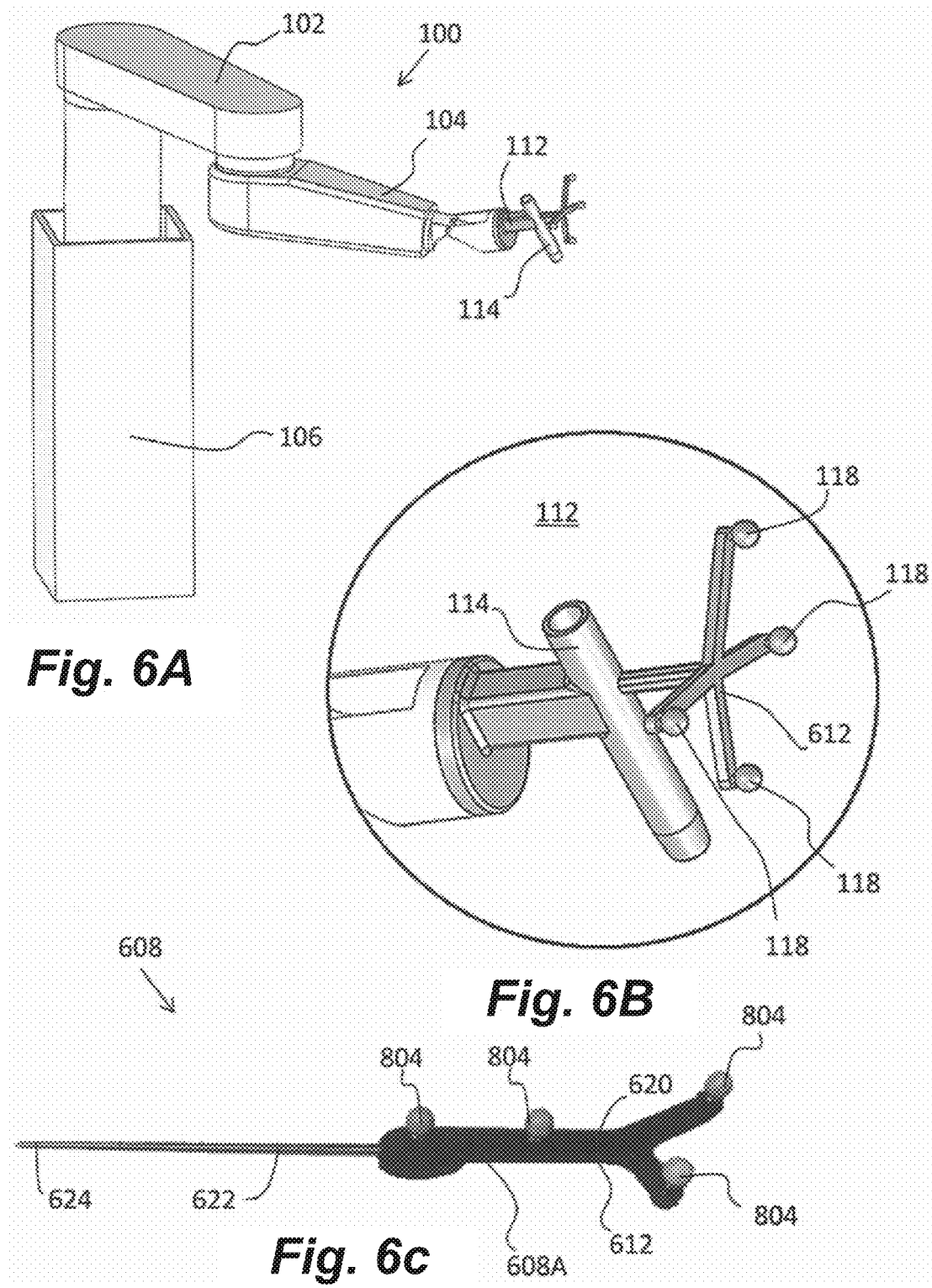

EXTENDED REALITY SYSTEMS FOR VISUALIZING AND CONTROLLING OPERATING ROOM EQUIPMENT

CROSS-REFERENCE TO RELATED APPLICATIONS

The present application is a continuation application of U.S. patent application Ser. No. 17/476,689 filed on Sep. 16, 2021, which is incorporated in its entirety herein.

FIELD

The present disclosure relates to surgical operating room equipment operations and computer assisted navigation of equipment and operators during surgery.

BACKGROUND

Surgical operating rooms can contain a diverse range of medical equipment, which can include computer assisted surgical navigation systems, surgical robot systems, medical imaging devices (e.g., computerized tomography (CT) scanners, magnetic resonance imaging scanners, fluoroscopy imaging, etc.), neuromonitoring equipment, patient monitors, microscopes, anesthesia equipment, etc.

A computer assisted surgical navigation system can provide a surgeon with computerized visualization of the present pose of a surgical tool relative to medical images of a patient's anatomy. Camera tracking systems for computer assisted surgical navigation typically use a set of cameras to track a tool reference array on a surgical tool which is being positioned by a surgeon during surgery relative to a patient reference array attached to a patient. The reference array, also referred to as a dynamic reference array (DRA) or dynamic reference base (DRB), allows the camera tracking system to determine a pose of the surgical tool relative to anatomical structure within a medical image and relative to the patient. The surgeon can thereby use real-time visual feedback of the determined pose(s) to navigate the surgical tool during a surgical procedure on the patient.

A surgical robot system can utilize optical tracking registered to a medical image as feedback for positioning a robotic arm while also visualizing instruments. The robotic arm includes an end effector which may be configured to guide a surgical tool used by a surgeon to perform a surgical procedure on a patient. Additionally, many surgical workflows with computer assisted surgical navigation systems and surgical robotic systems require x-rays or computerized tomography (CT) scans during operation and/or registration procedures.

In view of the number and diversity of medical equipment, attempting to position and control the medical equipment using numerous different user interfaces before and during a surgical procedure can become overly complex especially while attempting to maintain sterility by minimizing touching of surfaces of the medical equipment. Moreover, the medical equipment is usually controlled through physical interfaces which necessitate that operators be proximately located thereto, and the medical equipment displays are usually configured for contextual observation by operators proximately located thereto.

SUMMARY

Some embodiments of the present disclosure are directed to camera tracking systems and associated methods and computer program products that enable a remote operator who is wearing a remote extended reality (XR) headset to visualize and interact with three-dimensional (3D) computer images which are also viewable by another operator (local operator) who is wearing a local XR headset while performing a surgical procedure on a patient. Moreover, the remote operator wearing the remote XR headset may be able to visualize and control medical equipment that is remote from the remote operator during use of the medical equipment by the local operator.

In accordance with some embodiments, a camera tracking system that includes at least one processor (also referred to as "processor") is operative to receive patient reference tracking information indicating pose of a patient reference array tracked by a patient tracking camera relative to a patient reference frame. The processor determines a local XR headset view pose transform between a local XR headset reference frame of a local XR headset and the patient reference frame using the patient reference tracking information. The processor receives remote reference tracking information indicating pose of a remote reference array tracked by a remote reference tracking camera, and determines a remote XR headset view pose transform between a remote XR headset reference frame of a remote XR headset and the remote reference array using the remote reference tracking information. The processor transforms a 3D computer image from a local pose determined using the local XR headset view pose transform to a remote pose determined using the remote XR headset view pose transform which outputs a transformed 3D computer image, and provides the transformed 3D computer image to the remote XR headset for display with the remote pose relative to the remote XR headset reference frame.

Some other embodiments are directed to camera tracking systems and associated methods and computer program products that enable XR headsets to be used to visualize and control various types of medical equipments.

In accordance with some embodiments, a camera tracking system includes at least one processor ("processor") operative to receive equipment reference tracking information indicating poses of medical equipments and a patient reference array tracked by a tracking camera relative to a reference frame. The processor determines an XR headset view pose transform between an XR headset reference frame of an XR headset and the reference frame using the equipment reference tracking information. The processor obtains operator-gesture tracking information from the tracking camera indicating movement of an object relative to the XR headset reference frame by an operator wearing the XR headset. The processor selects an operational command from among a set of operational commands based on the operator-gesture tracking information, and provides instructions to one of the medical equipments based on the operational command that is selected.

Other camera tracking systems and corresponding methods and computer program products according to embodiments of the inventive subject matter will be or become apparent to one with skill in the art upon review of the following drawings and detailed description. It is intended that all such additional camera tracking systems, methods, and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIGS. 6A-6C respectively illustrate a surgical robot with an end-effector, an expanded view of the end-effector, and a surgical tool in accordance with some embodiments;

DETAILED DESCRIPTION

Figure 1:
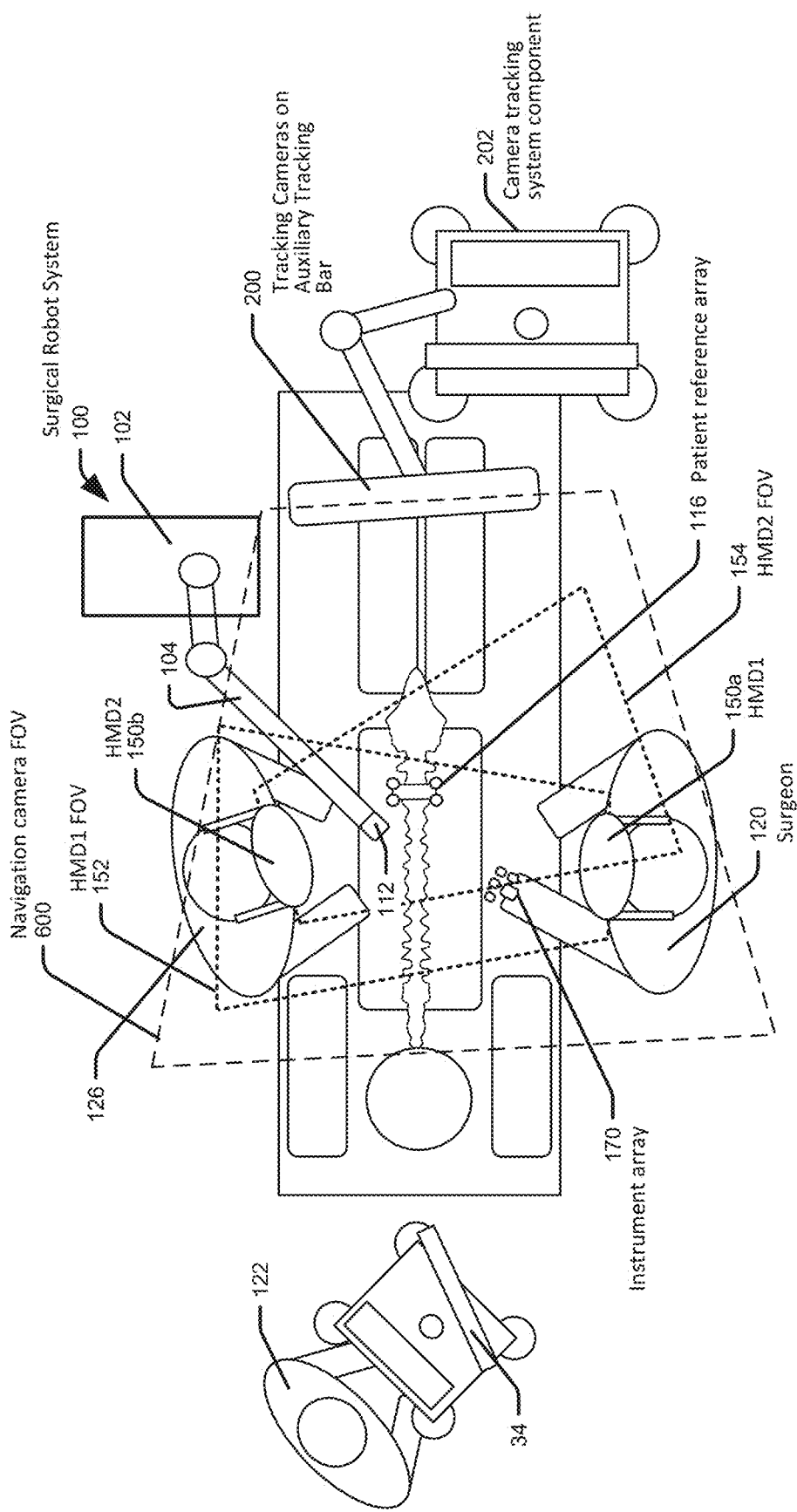
FIG. 1 is an overhead view of a potential arrangement for locations of a surgical robotic system including a surgical robot and tracking camera, and personnel wearing extended reality (XR) headsets during a surgical procedure, in accordance with some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
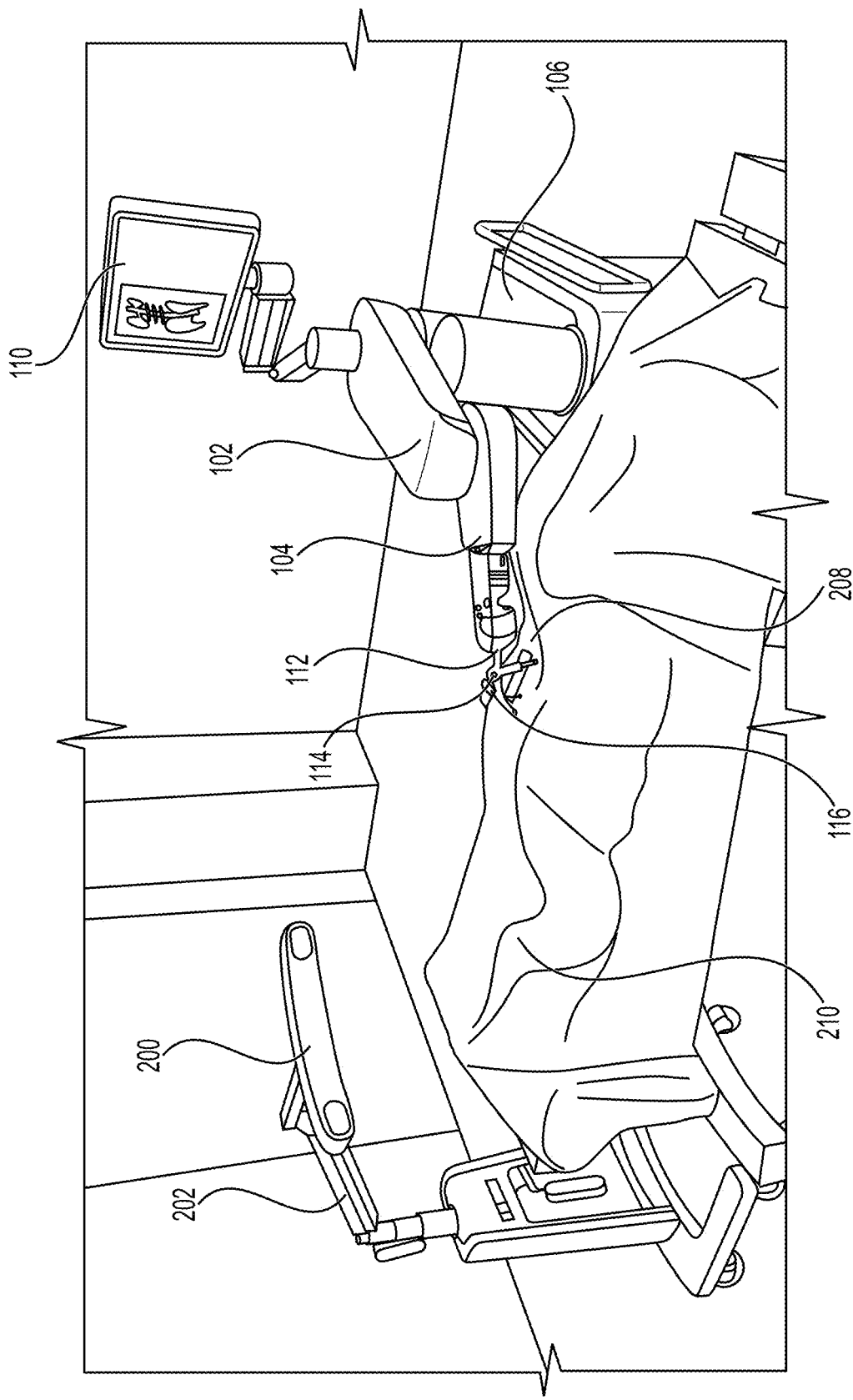
FIG. 2 illustrates the robotic system with the surgical robot and the camera positioned relative to the patient according to some embodiments.

Turning now to the drawing, FIGS. 1 and 2 illustrate a surgical robot system 100 in accordance with some embodiments. Surgical robot system 100 may include, for example, a surgical robot 102, one or more robot arms 104, a display 110, an end-effector 112, for example, including a guide tube 114, and an end effector reference array which can include one or more tracking markers. The surgical robot system 100 may include a patient reference array 116 with a plurality of tracking markers, which is adapted to be secured directly to the patient 210 (e.g., to a bone of the patient 210). Another reference array 170 is attached or formed on an instrument. The surgical robot system 100 may also utilize a tracking camera 200, for example, positioned on a camera tracking system component 202. The camera tracking system component 202 can have any suitable configuration to move, orient, and support the tracking camera 200 in a desired position, and may contain a computer operable to track pose of reference arrays. The tracking camera 200 may include any suitable camera or cameras, such as one or more infrared cameras (e.g., bifocal or stereophotogrammetric cameras), able to identify, for example, active and passive tracking markers for various reference arrays attached as the patient 210 (patient reference array), end effector 112 (end effector reference array), extended reality (XR) headset(s) 150a-150b worn by a surgeon 120 and/or a surgical assistant 126, etc. in a given measurement volume viewable from the perspective of the tracking camera 200. The tracking camera 200 may track markers 170 attached to an surgical tool or other instrument manipulated by a user. The tracking camera 200 may scan the given measurement volume and detect the light that is emitted or reflected from the reference arrays in order to identify and determine poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking camera 200 or other suitable device.

As will be explained in further detail below, in some embodiments the camera tracking system component 202 can operate to enable a remote operator who is wearing a remote XR headset to visualize and interact with 3D computer images which are also viewable by a local operator who is wearing a local XR headset, e.g., HMD1 150a and/or HMD2 150b, while performing a surgical procedure on the patient. In some further embodiments, the remote operator wearing the remote XR headset may be able to visualize and control medical equipment that is remote from the remote operator during use of the medical equipment by the local operator. In some additional or alternative embodiments, the camera tracking system component 202 can operate to enable the enable XR headset, e.g., HMD1 150a and/or HMD2 150b, to be used to visualize and control various types of medical equipments. The camera tracking system component 202 may be part of the surgical robot 102 or another system component.

The XR headsets 150a and 150b may each include tracking cameras that can track poses of reference arrays within their camera field-of-views (FOVs) 152 and 154, respectively. Accordingly, as illustrated in FIG. 1, the poses of reference arrays attached to various objects in the FOVs 152 and 154 of the XR headsets 150a and 150b and a FOV 600 of the tracking cameras 200, e.g., mounted to an auxiliary tracking bar.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The tracking camera 200 may be separated from the robot system 100 and positioned at the foot of patient 210. This location allows the tracking camera 200 to have a direct visual line of sight to the surgical field 208. Again, it is contemplated that the tracking camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200. The anesthesiologist 122 can operate anesthesia equipment which can include a display 34.

With respect to the other components of the robot 102, the display 110 can be attached to the surgical robot 102 and in other example embodiments, display 110 can be detached from surgical robot 102, either within a surgical room with the surgical robot 102, or in a remote location. End-effector 112 may be coupled to the robot arm 104 and controlled by at least one motor. In example embodiments, end-effector 112 can comprise a guide tube 114, which is able to receive and orient a surgical instrument 608 (described further herein) used to perform surgery on the patient 210.

As used herein, the term "end-effector" is used interchangeably with the terms "end-effectuator" and "effectuator element." The term "instrument" is used in a non-limiting manner and can be used interchangeably with "tool" to generally refer to any type of device that can be used during a surgical procedure in accordance with embodiments disclosed herein. Example instruments include, without limitation, drills, screwdrivers, saws, dilators, retractors, probes, implant inserters, and implants such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is operable to control the translation and orientation of the end-effector 112. The robot 102 is operable to move end-effector 112 under computer control along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively computer controlled). In some example embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some example embodiments, the pose of the surgical instrument can be dynamically updated so that surgical robot 102 can be aware of the pose of the surgical instrument at all times during the procedure. Consequently, in some example embodiments, surgical robot 102 can move the surgical instrument to the desired pose quickly without any further assistance from a surgeon.

As used herein, the term "pose" refers to the position and/or the rotational angle of one object (e.g., dynamic reference array, end-effector, surgical instrument, anatomical structure, etc.) relative to another object and/or to a defined coordinate system. A pose may therefore be defined based on only the multidimensional position of one object relative to another object and/or relative to a defined coordinate system, based on only the multidimensional rotational angles of the object relative to another object and/or to a defined coordinate system, or based on a combination of the multidimensional position and the multidimensional rotational angles. The term "pose" therefore is used to refer to position, rotational angle, or combination thereof.

In some further embodiments, surgical robot 102 can be configured to correct the path of a surgical instrument guided by the robot arm 104 if the surgical instrument strays from the selected, preplanned trajectory. In some example embodiments, surgical robot 102 can be configured to permit stoppage, modification, and/or manual control of the movement of end-effector 112 and/or the surgical instrument. Thus, in use, in example embodiments, a surgeon or other user can operate the system 100, and has the option to stop, modify, or manually control the autonomous movement of end-effector 112 and/or the surgical instrument.

Reference arrays can be formed on or connected to robot arm 104, end-effector 112, patient 210, and/or the surgical instrument to track poses in 6 degree-of-freedom (e.g., position along 3 orthogonal axes and rotation about the axes). In example embodiments, a reference array including a plurality of tracking markers can be provided thereon (e.g., formed-on or connected-to) to an outer surface of the robot 102, such as on robot 102, on robot arm 104, and/or on the end-effector 112. A patient reference array including one or more tracking markers can further be provided on the patient 210 (e.g., formed-on or connected-to). An instrument reference array including one or more tracking markers can be provided on surgical instruments (e.g., a screwdriver, dilator, implant inserter, or the like). The reference arrays enable each of the marked objects (e.g., the end-effector 112, the patient 210, and the surgical instruments 608) to be tracked by the tracking camera 200, and the tracked poses can be used to provide navigation guidance to a surgical procedure and/or used to control movement of the surgical robot 102 for guiding the end-effector 112 and/or an instrument attached to the robot arm 104. In example embodiments, the surgical robot system 100 can use tracking information collected from each of the reference arrays to calculate the pose (e.g., orientation and location), for example, of the end-effector 112, the surgical instrument 608 (e.g., positioned in the tube 114 of the end-effector 112), and the relative position of the patient 210.

Figure 3:
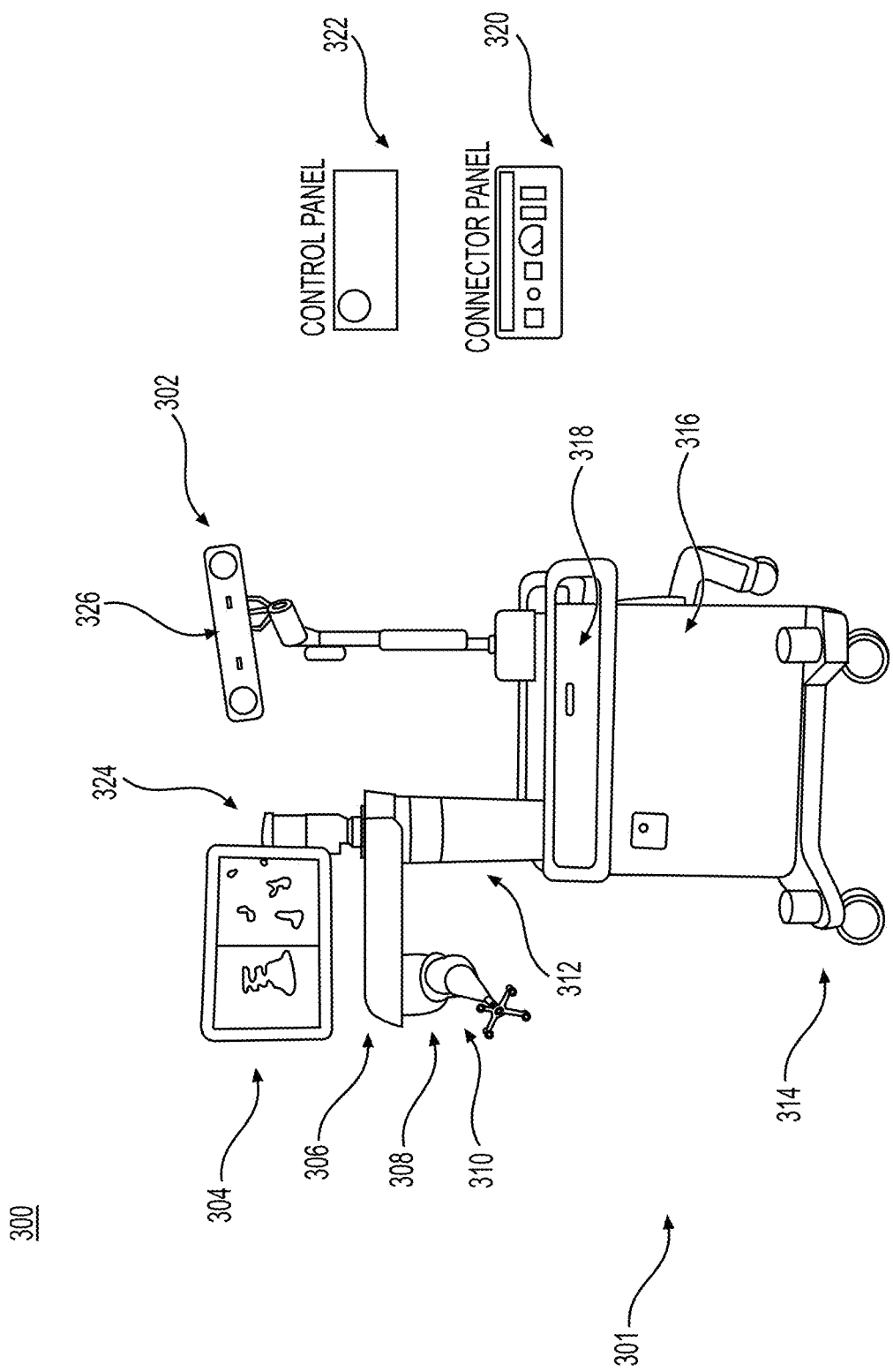
FIG. 3 illustrates a surgical robotic system in accordance with an example embodiment.

FIG. 3 illustrates further details of the surgical robot system 100 and tracking camera 200 of FIG. 1. Referring to FIG. 3 the surgical robot system 100 includes the surgical robot 102 including a display 110, upper arm 306, lower arm 308, end-effector 112, vertical column 312, casters 314, tablet drawer 318, and ring 324 which uses lights to indicate statuses and other information. The tracking camera 200 is supported by the camera tracking system component 202.

Figure 4:
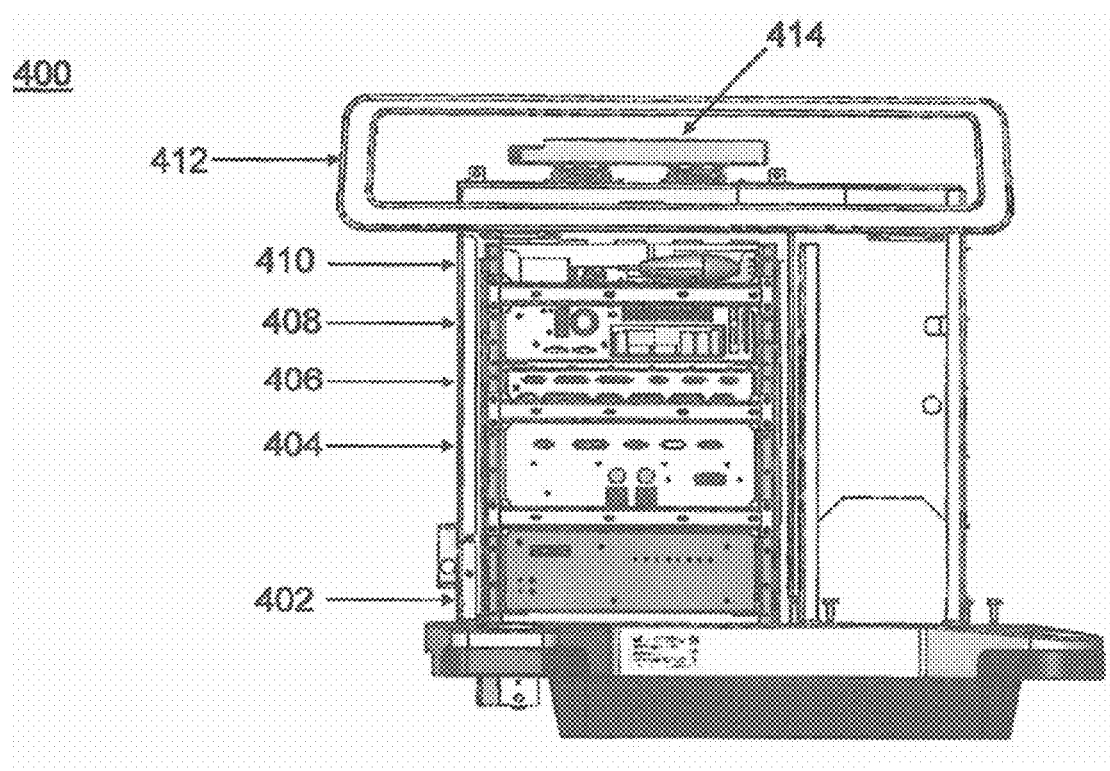
FIG. 4 illustrates electronic components of a surgical robot in accordance with some embodiments.

FIG. 4 illustrates a base 400 which may be a portion of surgical robot system 100 and cabinet 106. Cabinet 106 may house certain components of surgical robot system 100 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
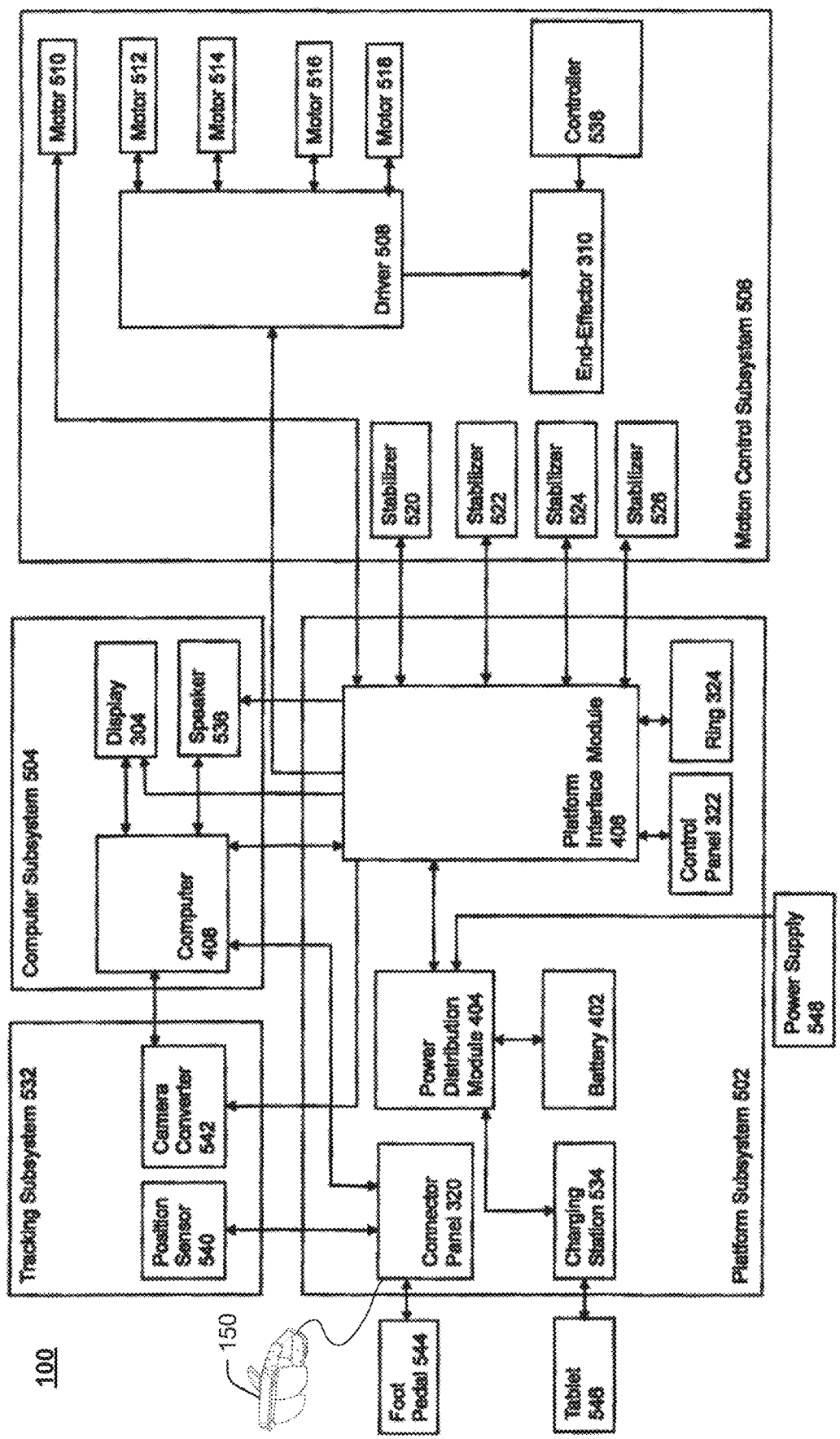
FIG. 5 illustrates a block diagram of electronic components of a surgical robot in accordance with some embodiments.

FIG. 5 illustrates a block diagram of certain components of an example embodiment of surgical robot system 100. Surgical robot system 100 may include platform subsystem 502, computer subsystem 504, motion control subsystem 506, and tracking subsystem 532. Platform subsystem 502 may further include battery 402, power distribution module 404, platform interface board module 406, and tablet charging station 534. Computer subsystem 504 may include computer 408, display 110, and speaker 536. Motion control subsystem 506 may include driver circuit 508, motors 510, 512, 514, 516, 518, stabilizers 520, 522, 524, 526, end-effector 112, and controller 538. Tracking subsystem 532 may include position sensor 540 and camera converter 542. System 100 may include a foot pedal 544 that can be actuated to control movement of the end effector 112, e.g., stop-start and/or regulate speed of movement, and tablet computer 546 which provides a touch-display interface for operators of the surgical robot system 100.

Input power is supplied to surgical robot system 100 via a power supply 548 which may be provided to power distribution module 404. Power distribution module 404 receives input power and is configured to generate different power supply voltages that are provided to other modules, components, and subsystems of surgical robot system 100. Power distribution module 404 may be configured to provide different voltage supplies to platform interface board module 406, which may be provided to other components such as computer 408, display 110, speaker 536, driver circuit 508 to, for example, power motors 512, 514, 516, 518 and end-effector 112, motor 510, ring 324, camera converter 542, and other components for surgical robot system 100 for example, fans for cooling the electrical components within cabinet 106.

Power distribution module 404 may also provide power to other components such as tablet charging station 534 that may be located within tablet drawer 318. Tablet charging station 534 may be in wireless or wired communication with tablet 546 for charging tablet 546. Tablet 546 may be used by a surgeon consistent with the present disclosure.

Power distribution module 404 may also be connected to battery 402, which serves as temporary power source in the event that power distribution module 404 does not receive power from power supply 548. At other times, power distribution module 404 may serve to charge battery 402 if necessary.

Other components of platform subsystem 502 may also include connector panel 320, control panel 322, and ring 324. Connector panel 320 may serve to connect different devices and components to surgical robot system 100 and/or associated components and modules. Connector panel 320 may contain one or more ports that receive lines or connections from different components. For example, connector panel 320 may have a ground terminal port that may ground surgical robot system 100 to other equipment, a port to connect foot pedal 544 to surgical robot system 100, a port to connect to tracking subsystem 532, which may comprise position sensor 540, camera converter 542, and cameras 326 associated with camera tracking system component 202. Connector panel 320 may also include other ports to allow USB, Ethernet, HDMI communications to other components, such as computer 408. In accordance with some embodiments, connector panel 320 may provide a wireless (e.g., WiFi 802.11, cellular 4G, 5G, NR, etc.) and/or wired communication connection with extended reality (XR) headsets 150 (e.g., 150a and 150b in FIG. 1) worn by the surgeon 120, surgical assistant 126, anesthesiologist 122, and/or the nurse or scrub tech 124, etc.

Control panel 322 may provide various buttons or indicators that control operation of surgical robot system 100 and/or provide information regarding surgical robot system 100. For example, control panel 322 may include buttons to power on or off surgical robot system 100, lift or lower vertical column 312, and lift or lower stabilizers 520-526 that may be designed to engage casters 314 to lock surgical robot system 100 from physically moving. Other buttons may stop surgical robot system 100 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of surgical robot system 100 of different modes that surgical robot system 100 is operating under and certain warnings to the user.

Computer subsystem 504 includes computer 408, display 110, and speaker 536.

Computer 504 includes an operating system and software to operate surgical robot system 100. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 540 and camera converter 542. Tracking subsystem 532 may correspond to camera tracking system component 202 including tracking camera 200 as described with respect to FIG. 3. Position sensor 540 may be tracking camera 200. Tracking subsystem may track the pose of certain markers that are located on the different components of surgical robot system 100 and/or instruments used by a user during a surgical procedure. This tracking may be conducted in a manner consistent with the present disclosure including the use of infrared technology that tracks the pose of active or passive elements, such as LEDs or reflective markers, respectively. The pose of structures having these types of markers may be provided to computer 408 which may be shown to a user on display 110. For example, a surgical instrument having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 112. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 112 in a manner such that one may control the roll and one may control the tilt, thereby providing multiple angles that end-effector 112 may be moved. These movements may be achieved by controller 538 which may control these movements through load cells disposed on end-effector 112 and activated by a user engaging these load cells to move surgical robot system 100 in a desired manner.

Moreover, surgical robot system 100 may provide for automatic movement of vertical column 312, upper arm 306, and lower arm 308 through a user indicating on display 110 (which may be a touchscreen input device) the pose of a surgical instrument or component on three dimensional image of the patient's anatomy on display 110. The user may initiate this automatic movement by stepping on foot pedal 544 or some other input means.

Turning now to FIGS. 6A-6C, the surgical robot system 100 relies on accurate positioning of the end-effector 112, surgical instruments 608, and/or the patient 210 (e.g., patient reference array 116) relative to the desired surgical area. In the embodiments shown in FIGS. FIGS. 6A-6C, the reference arrays include tracking markers 118, 804 which are rigidly attached to a portion of the instrument 608 and/or end-effector 112.

FIG. 6A depicts part of the surgical robot system 100 with the robot 102 including base 106, robot arm 104, and end-effector 112. The other elements, not illustrated, such as the display, marker tracking cameras, etc. may also be present as described herein. FIG. 6B depicts a close-up view of the end-effector 112 with guide tube 114 and a reference array that includes a plurality of tracking markers 118 rigidly affixed to the end-effector 112. In this embodiment, the plurality of tracking markers 118 are attached to the end-effector 112 configured as a guide tube. FIG. 6C depicts an instrument 608 (in this case, a probe) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screwdriver, an insertion instrument, a removal instrument, or the like.

In FIG. 6C, the reference array 612 functions as the handle 620 of the instrument 608. Four markers 804 are attached to the handle 620 in a manner that is out of the way of the shaft 622 and tip 624. Stereophotogrammetric tracking by the tracking camera 200 of these four markers 804 allows the instrument 608 to be tracked as a rigid body and for the system 100 to precisely determine the location of the tip 624 and the orientation of the shaft 622 while the instrument 608 is moved within view of tracking camera 200.

To enable automatic tracking of one or more instruments 608, end-effector 112, or other object to be tracked in 3D (e.g., multiple rigid bodies), the markers 118, 804 on each instrument 608, end-effector 112, or the like, may be arranged asymmetrically with a known inter-marker spacing. The reason for asymmetric alignment is so that it is unambiguous which marker 118, 804 corresponds to a particular pose on the rigid body and whether markers 118, 804 are being viewed from the front or back, i.e., mirrored. For example, if the markers 118, 804 were arranged in a square on the instrument 608 or end-effector 112, it would be unclear to the system 100, 300, 600 which marker 118, 804 corresponded to which corner of the square. For example, for the instrument 608, it would be unclear which marker 804 was closest to the shaft 622. Thus, it would be unknown which way the shaft 622 was extending from the array 612. Accordingly, each array 612 and thus each instrument 608, end-effector 112, or other object to be tracked should have a unique marker pattern to allow it to be distinguished from other instruments 608 or other objects being tracked.

Asymmetry and unique marker patterns allow the tracking camera 200 and system 100 to detect individual markers 118, 804 then to check the marker spacing against a stored template to determine which instrument 608, end-effector 112, or another object they represent. Detected markers 118, 804 can then be sorted automatically and assigned to each tracked object in the correct order. Without this information, rigid body calculations could not then be performed to extract key geometric information, for example, such as instrument tip 624 and alignment of the shaft 622, unless the user manually specified which detected marker 118, 804 corresponded to which position on each rigid body.

Figure 7A:
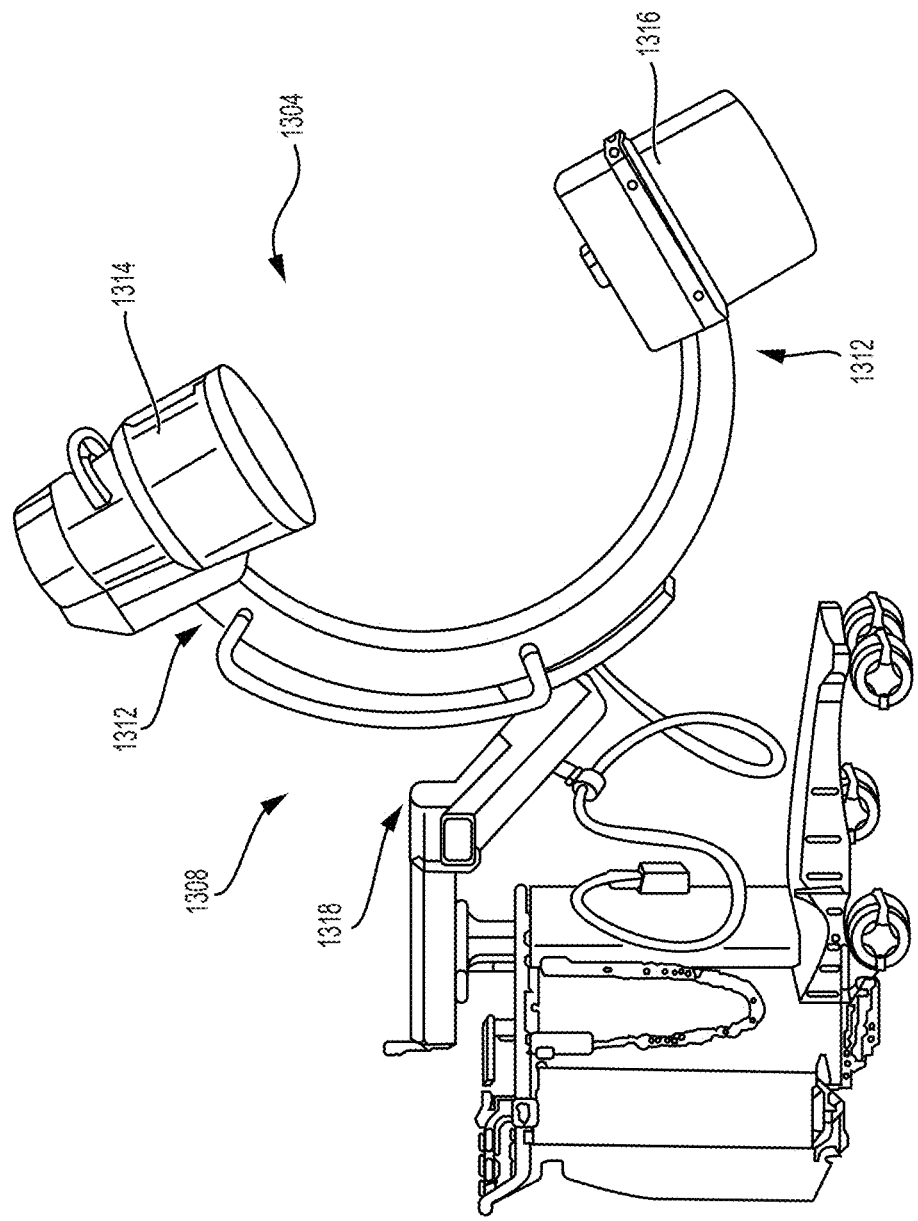
FIGS. 7A-7B respectively illustrate a C-arm image device and an O-arm imaging device in accordance with some embodiments.
Figure 7B:
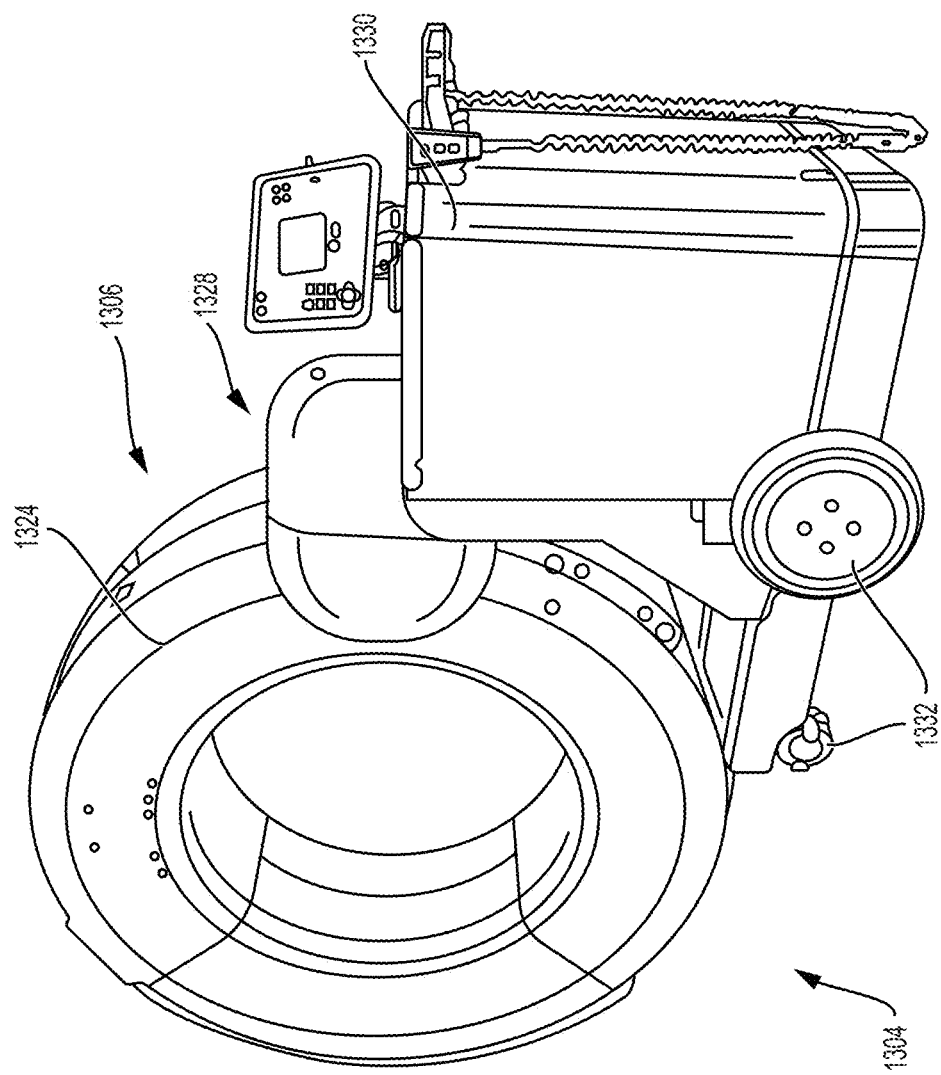

FIGS. 7A and 7B illustrate medical imaging systems 1304 that may be used in conjunction with robot system 100 and/or navigation systems to acquire pre-operative, intraoperative, post-operative, and/or real-time image data of patient 210. Any appropriate subject matter may be imaged for any appropriate procedure using the imaging system 1304. The imaging system 1304 may be any imaging device such as a C-arm 1308 device, an O-arm 1306 device, a fluoroscopy imaging device, a magnetic resonance imaging scanner, etc. It may be desirable to take x-rays of patient 210 from a number of different positions, without the need for frequent manual repositioning of patient 210 which may be required in an x-ray system. As illustrated in FIG. 7A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 7B, the imaging system 1304 may include an O-arm imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Using XR Headset for Remote Assistance and Controlling Medical Equipment

As was explained above, the numbers and diversity of medical equipment which can be present in an operating room can make it complex to properly position and control the equipment through numerous different user interfaces before and during a surgical procedure. Moreover, the medical equipment is usually controlled through physical user interfaces which necessitate that operators be proximately located thereto, and there is a need to minimize or avoid unnecessary touching of physical user interfaces in order to maintain sterility.

Some embodiments of the present disclosure are directed to camera tracking systems and associated methods and computer program products that enable a remote operator who is wearing a remote XR headset to visualize and interact with 3D computer images which are also viewable by another operator (local operator) who is wearing a local XR headset while performing a surgical procedure on a patient. Moreover, the remote operator wearing the remote XR headset may be able to visualize and control medical equipment that is remote from the remote operator during surgical use of the medical equipment by the local operator.

An XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. Thus, the term XR headset can referred to as an AR headset and/or a VR headset.

Remote Assistance and Training via XR and Machine Vision Navigated Surgery

Navigated surgery introduces tracking information which is not present in traditional surgeries, but the addition of timestamped and synchronized sensor-rich XR headsets and visible light machine vision (MV) navigation systems enables users to be visually provided with a information-rich environment during pre-operative planning and inter-operative performance of a surgical procedure.

Various embodiments are explained that connect, share, interface and manipulate information generated by medical equipment and/or user operators in such a way that remote surgical assistance, training and procedure reviews can be greatly improved.

These embodiments may enable visualizing, manipulating, sharing and prioritizing relevant information in such a way that user operators not physically present in the operating room or testing lab can feel a sense of connectivity and immersion as if they were local during the surgical procedure. This increased connectivity and immersion greatly increases the effectiveness of user operators providing remote assistance to surgeons, surgical assistants, etc. while also greatly improving the potential of remote training applications.

Although various embodiments are described in the context of orthopedic surgery, they are not limited to any type of surgery. Moreover, the embodiments are not limited to using visible light optical tracking sensors, but instead can be operate with tracking information provided by inertial sensors, etc.

Various embodiments are now described with reference to FIG. 8.

Figure 8:
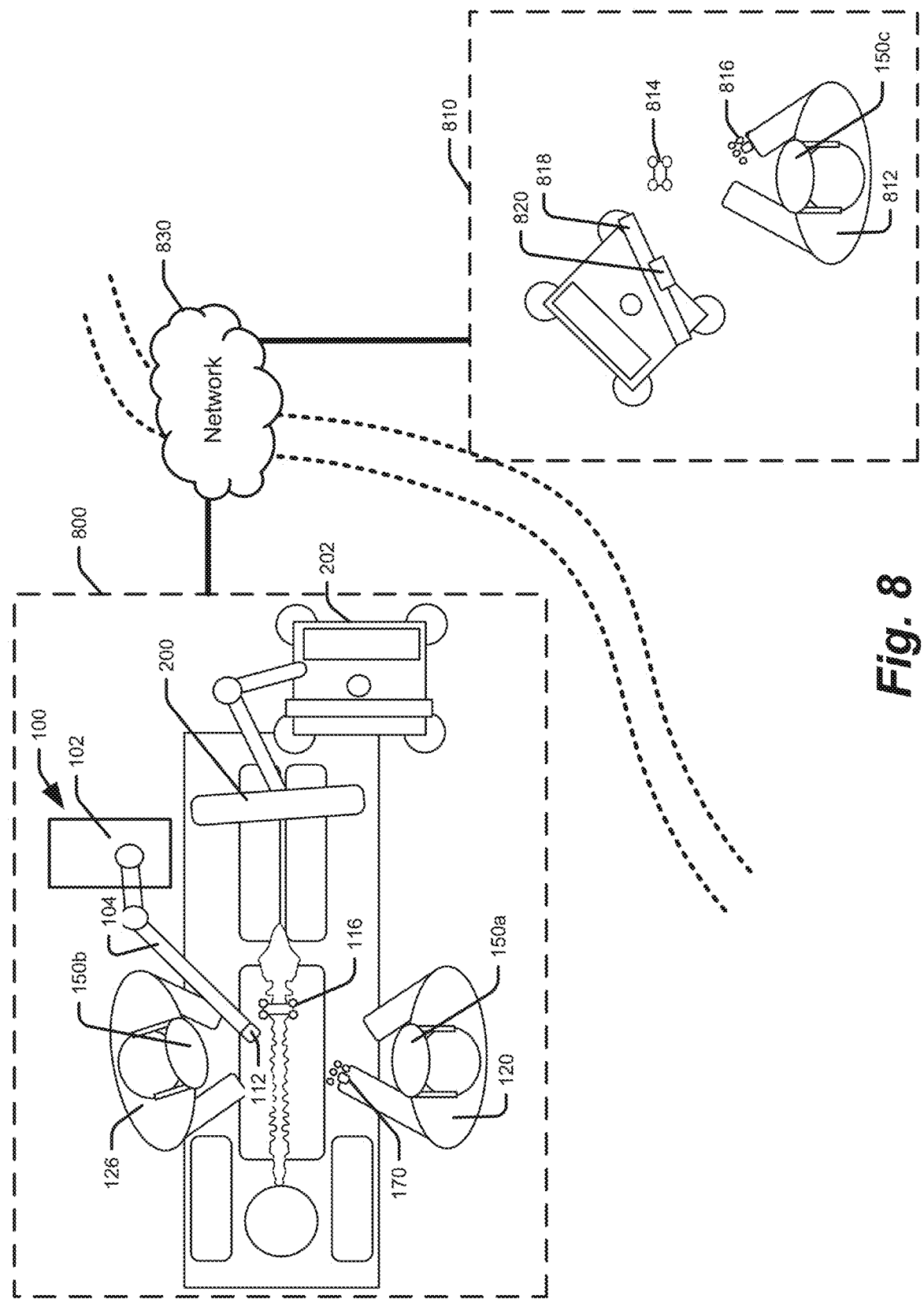
FIG. 8 illustrates an overhead view of a local arrangement of equipment and remote arrangement of equipment enabling a remote operator who is wearing a remote XR headset to visualize and interact with 3D computer images which are also viewable by a local operator who is wearing a local XR headset while performing a surgical procedure on a patient, in accordance with some embodiments.

FIG. 8 illustrates an overhead view of a local arrangement of equipment in a local environment 800, such as an operating room, and remote arrangement of equipment in a temporally and/or spatially separated remote environment 810 where a remote operator 812 who is wearing a remote XR headset 150c is operationally able to visualize and interact with 3D computer images which are also viewable by a local operator, e.g., surgeon 120, surgical assistant 126, etc. who is wearing a local XR headset 150a, 150b, etc. while performing a surgical procedure on a patient, in accordance with some embodiments. The remote XR headset 150c can include tracking cameras that operate to track poses of a remote reference array 814 and an instrument reference array 816. Alternatively additionally, another tracking camera can be proximately located to the remote operator 812 to tracking poses of tracking arrays which, for example, are within the field-of-view of the remote operator 812. The remote operator 812 may view information displayed on a physical display device 818 which may include a microphone 820. In accordance with some embodiments, a camera tracking system is communicatively connected to at least some of the local equipment in the local environment 800 (e.g., OR) and at least some of the remote equipment in the remote environment 810 through at least one network, e.g., private or public network such as the Internet. The camera tracking system may be part of the camera tracking system component 202, the surgical robot 102, and/or another component residing in the local environment 800, the remote environment 810, and/or another location connected to the network 820.

Moreover, the remote operator 812 wearing the remote XR headset 150c may be able to visualize and control medical equipment in the local environment 800 during use of the medical equipment by the local operator 120, 126, etc.

As used herein, the term "remote" signifies an operator who is not physically present in the operating room (OR) or testing lab in the (1) spatial sense (2) temporal sense or both (3) spatial and temporal sense. This means that communication can be real-time with a remote operator at another location (1) or information can be recorded for playback and analysis in the cases of (2) and (3). Generally speaking, remote operators of type (1) are more likely to be providing technically assistance or expert support while (2) and (3) are more likely to be for either training purposes of for after-the-fact issue analysis (e.g., technical problem reporting).

The camera tracking system may use tracking information and other information from multiple XR headsets 150a and 150b such as inertial tracking information and optical tracking information as well as (optional) microphone information. The XR headsets 150a and 150b operate to display visual information and play-out audio information to the wearer. This information can be from local sources (e.g., the surgical robot 102, and other medical equipment in the local environment 800), remote sources (e.g., patient medical image server), and/or other electronic equipment. The XR headsets 150a and 150b track apparatus such as instruments, patient references and end effectors in 6 degrees-of-freedom (6DOF). They also track the hands of the wearer by tracking the position of, e.g., 24 recognizable points on the hands. The XR headsets 150a and 150b may also operate to track hand poses and gestures to enable gesture based interactions with "virtual" buttons and interfaces displayed through the XR headsets 150a and 150b and can also interpret hand or finger pointing or gesturing as various defined commands. Additionally, the XR headsets 150a and 150b may have a 1-10× magnification digital color camera sensor called a digital loupe.

As explained above, there can be, and often is, an "outside-in" machine vision navigation bar (tracking cameras 200) in the local environment 800. The navigation bar tracks instruments and may include a color camera. The machine vision navigation bar generally has a more stable view of the environment because it does not move as often or as quickly as the XR headsets 150a and 150b tend to move while positioned on wearers' heads. The patient reference array 116 is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150a and 150b.

In some embodiments, one or more of the XR headsets 150a and 150b are minimalistic XR headsets that display local or remote information but include fewer sensors and are therefore more lightweight.

One or more 2D monitors (e.g., display 34 in FIG. 1) and computer systems may be provided in the local environment 800 for alternative touch, mouse, and/or keyboard interfaces that are also viewable by local individuals who are or are not wearing XR headsets. These 2D monitors may or may not be draped for sterility purposes.

In addition to live and recorded sensor information, there is also important local information in the form of the current software state located in, e.g., a navigation controller or cloud server. For example, a navigation "plan" for navigated implanting of screws and/or other devices may be viewed and adapted om navigation guidance information that is provided to the XR headsets 150a and 150b and/or 2D monitor for display.

The machine vision cameras may generate color video streams of the patient, cadaver, phantom, etc. The patient, cadaver, phantom, etc. may also be reconstructed by any combination of machine vision and color cameras to generate a 3D surface model thereof.

In FIG. 8, the medical equipment within the local environment 800 is positioned locally adjacent to the patient and the human operators, e.g., surgeon, surgical assistance, trainee or support staff. In contrast, the remote equipment within the remote environment 810 is remotely located from local environment OR 800 and is not directly observable by the tracking cameras of the camera tracking system component 202 and/or of the local XR headsets 150a and 150b. The remote environment 810 may, for example be physically remote (e.g., the other side of the world) or temporally remote (e.g., in the same location but days later for training/visualization/understanding purposes).

In one embodiment, a minimum equipment confirmation for a remote environment 810 is a 2D monitor and user interface (e.g., touchscreen or mouse and keyboard) that enables a remote operator 812 to visualize and interact with 3D computer images which are also viewable by a local operator in the local environment 800 who is wearing a local XR headset 150a or 150b while performing a surgical procedure on a patient. For example, the remote operator 812 may view one or more color or monocular video streams generated by cameras in the local environment 800 via the network 830. In some embodiments, the remote operator 812 can also view the location of instruments relative to patient anatomy or CT scans. When the remote environment 810 is not temporally remote, the remote operator 812 can interact in real-time with the local operator(s), such as by graphically highlighting, marking-up, and/or modifying information that is displayed to the local operators 120, 128, etc. via the local XR headset 150a or 150b and/or a 2D display device.

For example, a surgical plan may be modified by the remote operator 812 in response to something seen by the remote operator 812 on the live views or feedback received from surgical robot 102 end effector 112 sensors or something seen in preoperative or intraoperative patient image scans. A minimum remote environment can be extended via the use of a microphone 820 and video camera sensors, e.g., in the remote XR headset 150c, which enhances communication by allowing local operators to hear and see guidance from the remote operator 812.

The potential of assistance and/or training applications can be significantly enhanced by the operations enabling the remote operator to view and visually interact through the remote XR headset 150c with information viewed by the local operator through the local XR headset 150a/150b and, vice versa, for the local operator to view information the local XR headset 150a/150b generated by the remote operator. The remote XR headset 150c may operate to track pose of an instrument array 816, e.g., stylus array, which may be manipulated by the remote operator 812 to generate graphical information that is provided to the local operator for viewing through the local XR headset 150a/150b.

With digital information being shared between the remote environment 810 and the local environment 800 via the network 830, spatial information can be transformed, presented and manipulated in visually meaningful, intuitive and useful coordinate systems.

In some embodiments, the local XR headsets 150a and 150b and the remote XR headset 150c are each tracked in "locally level" coordinate systems using accelerometers in the respective headsets, which enables tracking to be performed relative to gravity. Gravity (pitch and roll) is presumed to be constant across the remote environment 810 and the local environment 800. Because of this, a single 4DOF (X, Y, Z position and heading) transformation can be applied for transformations relating to the remote XR headset 150c so that the displayed content is configured to float in front of the remote XR headset 150c in roughly the same location as the same content is displayed through the local XR headsets 150a and 150b.

At least one processor can configured to receive tracking information from tracking cameras which identifies poses of tracked reference arrays relative to various defined reference frames, which may include the following:
1) p-frame: local patient reference frame;
2) v-frame: the remote (or virtual) reference frame;
3) s-frame: the local XR headset 150a/150b reference frame (e.g., for a surgeon or assistance wearing the local XR headset 150a/150b while performing a medical procedure on the patient); and
4) a-frame: the remote XR headset 150c reference frame (e.g., for a remote surgeon, assistance, or trainee wearing the remote XR headset 150c while viewing information relating to the medical procedure on the patient).

The 6DOF affine transformation between the s and p frames are estimated by the local tracking apparatus as are the transformations between the a and v frames. The 6DOF transformations are referred to as $T^P_s$ and $T^v_a$, respectively. In some embodiments, accelerometers in the remote XR headset 150c enable the 3D content to be transformed from a pose for displaying through the local XR headset 150a/150b to a transformed pose for displaying through the remote XR headset 150c. Posing the 3D content in a desired location for remote user to view through the remote XR headset 150c may include posing the 3D content in front of the remote operator 812 (e.g., X and Y position) at an appropriate height (e.g., Z position) and with a desired heading or yaw (e.g., orientation about he up/down Z axis). Denoting the XYZ translation vectors as r and the heading angles as φ, measurements are then needed of rsp, rav, φsp, and φav.

The at least one processor ("processor") computes a difference in translation and heading between the local p-frame and the remote v-frame. When it is determined that a local XR headset 150a/150b is within a desired range of poses, the remote operator 812 may initiate computation, e.g., by pressing a button or performing a defined hand gesture which is tracked by a tracking camera (e.g., part of the remote XR headset 150c) to compute these 4-DOF deltas as follows:

$$\varphi_\delta = \varphi_{sp} - \varphi_{av}$$

$$r_\delta = r_{sp} - r_{av}$$

The remote XR headset 150c continues directly tracking $T^v_a$ directly as independent ray and Ray translation and direction cosine matrix components. The φ_δ and r_δ yaw and translation deltas are applied to the virtual content in order to make it appear in roughly the same location for local and remote XR headset wearers. If the remote operator 812 wants to see and interact with the content from a different perspective than the local operator 120/126, the remote operator 812 can initiate rotation of the content heading cps via a defined remote AR headset 150c command to create an angularly offset, such as on the opposite side of a virtual bed, and interact with the local operator 120/126 based on the angularly offset view.

With the operational ability to communicatively share all sensor, aligned tracking, and software state information between operators in the local and remote environments 800 and 810, communication among operators becomes highly intuitive. 2D screen sharing can include generating virtual 2D screens which are viewed through XR headsets in one or both environments 800 and 810. Virtual 2D screens can be generated for viewing the XR headsets to show the state of the other environment's 2D monitor or general information. For example, remote operator 812 can view through remote XR headset 150c a virtual 2D screen showing information generated for medical equipment within local environment 800 and vice versa. The shared information can include, without limitation, annotations and mark-ups of medical imagery, annotations or markups of still images captured from sensors, video chat feeds or 2D renderings of remote AR content, etc.

The remote operator 812 wearing the remote XR headset 150c can be operationally provided multiple XR specific ways of interacting with the local operator 120/126. For example, a tool reference array 816, e.g., on a stylus, can be used and shown as a "remote stylus" or "remote hand" via virtual content displayed on the local XR headset 150a/150b and/or on the 2D local display in the local environment 800. A virtual representation of the remote user's head location can also be displayed on the local XR headset 150a/150b and/or on the 2D local display in the local environment 800 for improved social interaction (e.g., nodding, head shaking or exact perspective become intuitively apparent). With the ability to point out detailed information or draw 3D virtual mark-ups via stylus (e.g., where to make incisions or place a quatrospike), point or gesture with hands and head without temporal and physical proximity restriction, a remote operator 812 (e.g., experts or clinical representatives) can be virtually present in the OR and offer live support.

In some embodiments, live data feeds of digital information are shared between the local and remote environments 800 and 810 during navigated procedures, which can enhance communication between on-site and remote staff and allows for improved training and assistance during and after surgeries. Examples of digital information which can be shared include:
  a. Navigation video feeds: automated diagnostic and information mark-ups draw attention to important information, views show everything that the navigation cameras can see and are in visible light.
  b. Color navigation view and digital loupe: a live perspective of the navigation camera as well as what the surgeon/physician's assistant is looking at in full color and high resolution.
  c. Instrument and end effector tracking: enables the remote operator to see in 3D where all instruments, end effectors and other surgical apparatus are in real-time.
  d. Remote "stylus" tracking: allows remote operator to point out objects with an accurately tracked stylus pose.
  e. Hand tracking: allows remote operator to point out objects using hand gestures in an intuitive manner.
  f. Head tracking: allow local and remote operators to visually observe where each other is looking relative to the patient and medical equipment.
  g. Plan information, timers, notes checklists and metadata: synchronizing such information via the network 830 enable the remote operator 812 to know the state of the planned versus executed surgery at all times and update plans or details accordingly.

h. CT data and other medical imagery: important CT and other 2D and 3D medical imagery can be viewed and marked-up in real-time (data may include planned implant placement) by the remote operator 812 via the remote XR headset 812.

i. 3d surface reconstructions: reconstructions of the scene in 3d via machine vision cameras can add to the information and sense of immersion or perspective of the remote operator 812.

The remote operator 812 may directly remotely control medical equipment in the local environment 800 and/or provide textual and/or graphical recommendations/instructions to the local operator(s) 120 and 126 via hand gestures and/or movement of the instrument (stylus) reference array 816 tracked by the remote XR headset 150c and/or another tracking camera.

Various camera tracking systems are now described which transform the local XR headset 150a/150b view of a 3D computer image for display through the remote XR headset 150c relative to the remote reference array 814.

Figure 9:
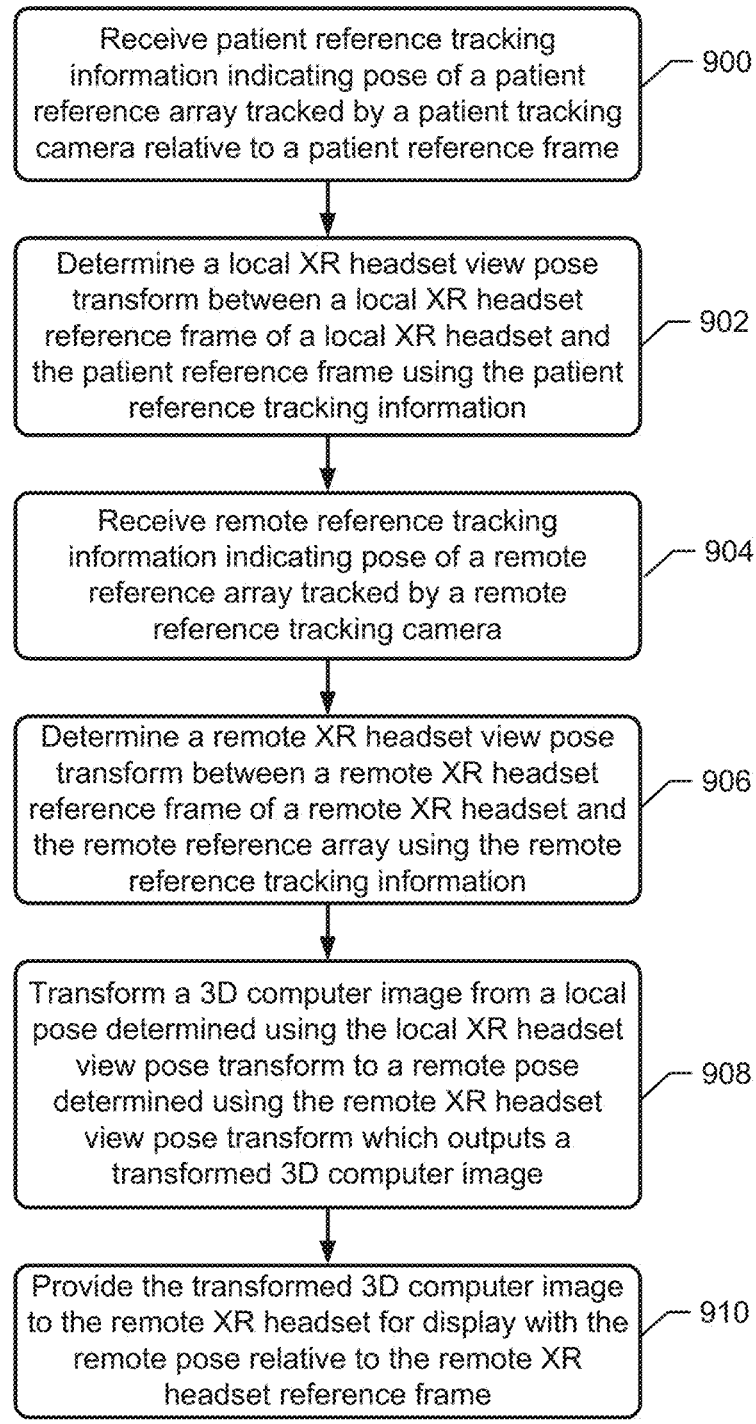
FIG. 9 is a flowchart of operations by a camera tracking system for enabling a remote operator wearing a remote XR headset to visualize and interact with 3D computer images which are also viewable by a local operator wearing a local XR headset while performing a surgical procedure on a patient, in accordance with some embodiments.

FIG. 9 is a flowchart of operations by a camera tracking system for enabling a remote operator wearing a remote XR headset 150c to visualize and interact with 3D computer images which are also viewable by a local operator wearing a local XR headset 150a/150b while performing a surgical procedure on a patient, in accordance with some embodiments.

Referring to FIG. 9, camera tracking system includes at least one processor ("processor" for brevity) operative to receive 900 patient reference tracking information indicating pose of a patient reference array 116 tracked by a patient tracking camera 200 relative to a patient reference frame 116. The processor is further operative to determine 902 a local XR headset view pose transform between a local XR headset reference frame of a local XR headset 150a/150b and the patient reference frame using the patient reference tracking information. The processor is further operative to receive 904 remote reference tracking information indicating pose of a remote reference array 814 tracked by a remote reference tracking camera, e.g., part of remote XR headset 816). The processor is further operative to determine 906 a remote XR headset view pose transform between a remote XR headset reference frame of a remote XR headset 150c and the remote reference array using the remote reference tracking information. The processor is further operative to transform 908 a 3D computer image from a local pose determined using the local XR headset view pose transform to a remote pose determined using the remote XR headset view pose transform which outputs a transformed 3D computer image. The processor is further operative to provide 910 the transformed 3D computer image to the remote XR headset 150c for display with the remote pose relative to the remote XR headset reference frame.

The processor may be further operative to transform the 3D computer image from the local pose to the remote pose while the patient tracking camera is remote from the remote reference tracking camera 150c and not positioned to track pose of the remote reference array 814, and while the remote reference tracking camera 150c is not positioned to track pose of the patient reference array 116, e.g., because the local environment 800 and the remote environment 810 are spatially and/or temporarily offset.

As explained above, a 4 degree-of-freedom (DOF) transformation can be used instead of a 6 DOF transformation using an accelerometer matters in the local and remote XR headsets 150a/150b and 150c and an assumption that the local and remote environments 800 and 810 are subject to the same gravity vector. Using a 4 DOF transformation can substantially reduce the computing and memory resources that would otherwise be required for performing a 6 DOF transformation at a frequency that allows real-time update of displayed information.

Accordingly, in one embodiment the processor is further operative to determine a 4 DOF pose of the remote XR headset based on measured movement along three orthogonal axes of the remote XR headset reference frame and rotation about one of the three orthogonal axes aligned with gravitational direction. The operation to transform the 3D computer image from the local pose determined using the local XR headset view pose transform to the remote pose determined using the remote XR headset view pose transform, includes processing the 4 DOF pose of the remote XR headset through the remote XR headset view pose transform.

Figure 10:
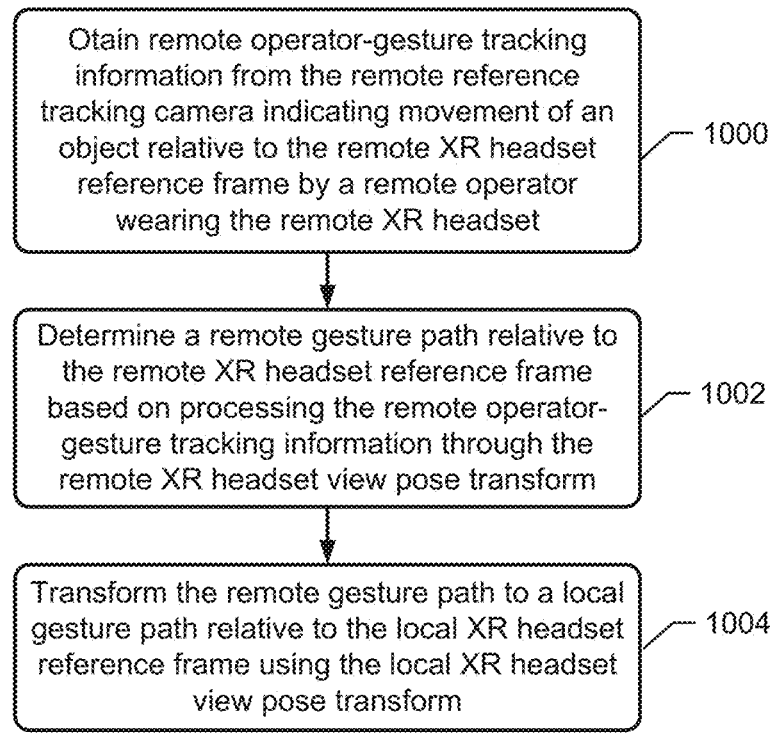
FIG. 10 is a flowchart of operations by a camera tracking system for transforming operator gestures tracked relative to the remote environment to corresponding gesture paths relative to the local environment, accordance with some embodiments.

Some further embodiments are directed to identifying a remote pose of a path gesture performed by a remote operator wearing the remote XR headset 150c relative to the remote XR headset reference frame, transforming the remote pose of the path gesture relative to the remote XR headset reference frame to a local pose relative to the local XR headset reference frame, and providing a computer generated indication of the path gesture with the local pose to the local XR headset 150a/150b for display relative to the patient reference array 116. FIG. 10 is a flowchart of corresponding operations that can be performed by a camera tracking system in accordance with some embodiments. Referring to FIG. 10 the processor of the camera tracking system is further operative to obtain 1000 remote operator-gesture tracking information from the remote reference tracking camera 150c indicating movement of an object 816 (e.g., tracked stylus, hand, etc.) relative to the remote XR headset reference frame by a remote operator 812 wearing the remote XR headset 150c. The processor determines 1002 a remote gesture path relative to the remote XR headset reference frame based on processing the remote operator-gesture tracking information through the remote XR headset view pose transform, and transforms 1004 the remote gesture path to a local gesture path relative to the local XR headset reference frame using the local XR headset view pose transform.

In some further embodiments, the processor provides the local gesture path to the local XR headset 150a/150b for display relative to the local XR headset reference frame.

In another embodiment, while the remote operator 812 is viewing the transformed 3D computer image displayed by the remote XR headset 150c, remote operator moves the object 816 to indicate a remote gesture path for viewing by the local operator 120/126. In one embodiment, the processor is further operative to determine 1002 the remote gesture path relative to the remote XR headset reference frame based on tracking movement indicated by the remote operator-gesture tracking information of a hand and/or a stylus which is moved by the remote operator 812 while concurrently viewing the transformed 3D computer image through the remote XR headset 150c relative to the hand and/or stylus being moved.

Some further embodiments, the remote operator 812 can move the hand and/or stylus to form a gesture which is recognized by the camera tracking system is corresponding to various defined operational commands, which can control equipment in the local environment 800, e.g., local to the patient reference frame. In one embodiment, the processor is further operative to select an operational command from among a set of operational commands based on the remote gesture path corresponding to defined gesture associated with the operational command, wherein the operational commands in the set are associated with different shaped gesture paths. The processor then provides the operational command to an equipment, e.g., surgical robot 102, which is local to the local XR headset.

Figure 11:
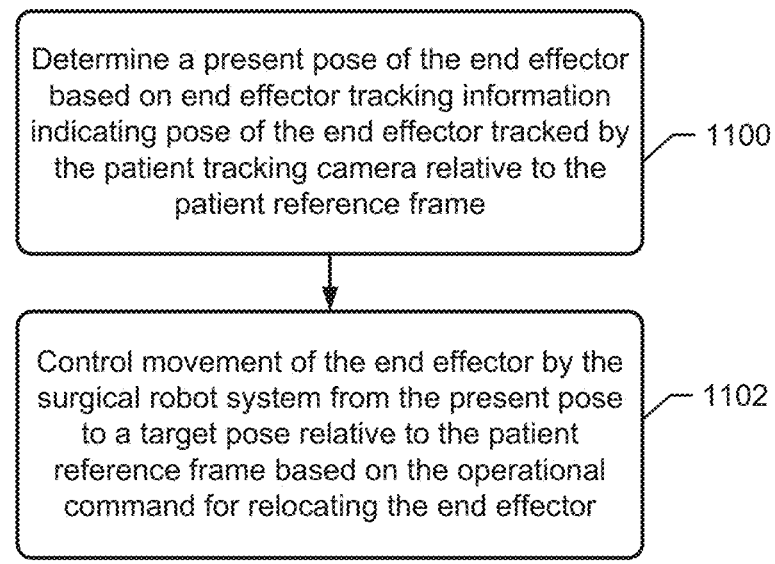
FIG. 11 is a flowchart of operations by a camera tracking system for controlling movement of an end effector of a surgical robot responsive to a hand/stylus gesture by a remote operator, in accordance with some embodiments.

In a further embodiment, the processor selects the operational command for relocating an end effector 112 connected to a surgical robot arm 104 that is movable under control of a surgical robot system 100, from among the set of operational commands based on the remote gesture path corresponding to the defined gesture associated with the operational command for relocating the end effector 112. FIG. 11 is a flowchart of operations by camera tracking system for controlling movement of an end effector 112 of a surgical robot 102 responsive to a hand/stylus gesture by a remote operator 812, in accordance with some embodiments. Referring to FIG. 11, the processor determines 1100 a present pose of the end effector 112 based on end effector tracking information indicating pose of the end effector 112 tracked by the patient tracking camera 200 relative to the patient reference frame. The processor controls 1102 movement of the end effector 112 by the surgical robot system 100 from the present pose to a target pose relative to the patient reference frame based on the operational command for relocating the end effector 112.

In a further embodiment, the processor determines a planned end effector trajectory path from the present pose to the target pose based on at least a segment of the remote gesture path. The processor controls movement of the end effector by the surgical robot system to conform to the planned end effector trajectory path from the present pose to the target pose.

The transformed 3D computer image may include a graphical representation of the end effector displayed based on the remote pose relative to the remote XR headset reference frame and include a graphical representation of anatomical structure of the patient displayed based on the remote pose relative to the remote XR headset reference frame. The processor may then be operative to determine a planned end effector 112 trajectory path from a present graphical pose of the graphical representation of the end effector 112 to a target graphical pose of the graphical representation of the end effector 112 based on tracking movement of fingers and/or a hand of the remote operator 812 wearing the remote XR headset 150c relative to the graphical representation of the end effector displayed relative to remote XR headset reference frame, and control movement of the end effector 112 by the surgical robot system 100 to conform to the planned end effector trajectory path from the present pose relative to the patient reference frame to the target pose relative to the patient reference frame.

In some further embodiments the processor is operative to select the operational command from among the set of operational commands which control at least one of the following:
1) operational settings of a computer assisted surgical navigation system;
2) operational settings of a surgical robot system;
3) operational settings of medical imaging equipment which is operable to obtain medical images of anatomical structure of the patient;
4) operational settings of intraoperative neuromonitoring equipment which is operable to monitor neural structures of the patient;
5) operational settings of the local XR headset;
6) operational settings of a computer display which is local to the local XR headset;
7) operational settings of a microscope which is local to the local XR headset;
8) operational settings of an exoscope which is local to the local XR headset;
9) operational setting of a lighting apparatus which is operable to illuminate the patient;
10) operational settings of a powered adjustable surgical bed which is operable to support the patient;
11) operational settings of a microscope which is local to the local XR headset;
12) operational settings of anesthesia equipment which is operable to supply anesthesia to the patient;
13) operational settings of a clock and/or timer which is local to the local XR headset;
14) operational settings of communication equipment which is local to the local XR headset; and
15) operational settings of sound equipment which is local to the local XR headset.

Figure 12:
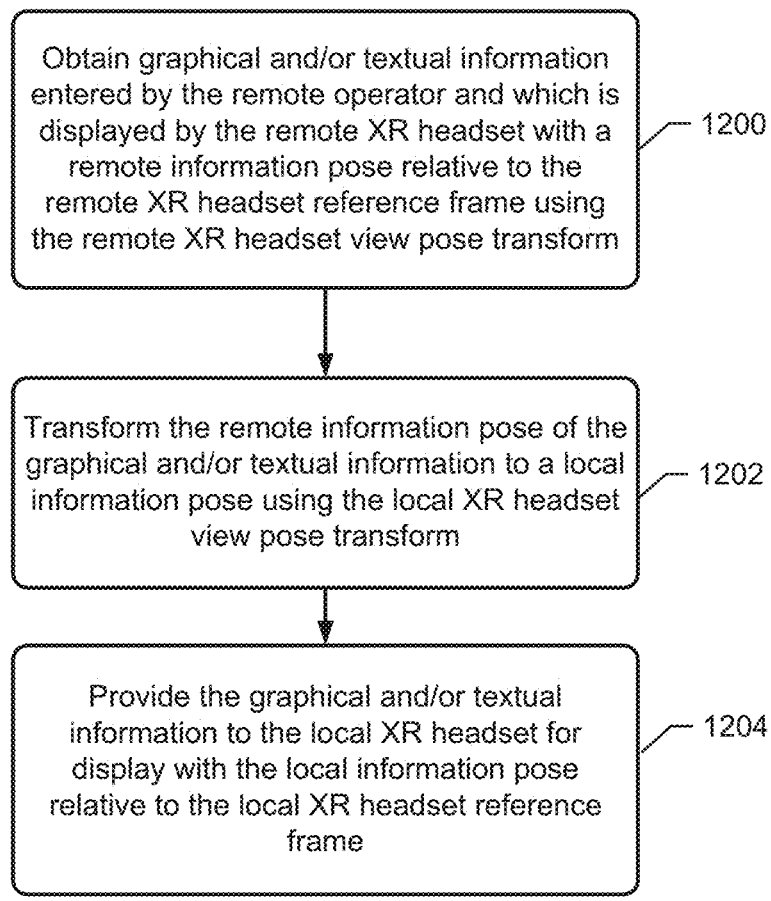
FIG. 12 is a flowchart of operations by a camera tracking system for transforming graphical and/or textual information which has been entered by a remote operator located in a remote environment to a pose which is displayed to a local operator wearing a local XR headset in a local environment, in accordance with some embodiments.

FIG. 12 is a flowchart of operations by camera tracking system for transforming graphical and/or textual information which has been entered by a remote operator 812 located in the remote environment 810 to a pose which is displayed to a local operator 120/126 wearing a local XR headset 150a/150b in a local environment, in accordance with some embodiments. Referring to FIG. 12, the processor is operative to obtain 1200 graphical and/or textual information entered by the remote operator 812 and which is displayed by the remote XR headset 150c with a remote information pose relative to the remote XR headset reference frame using the remote XR headset view pose transform. The processor transforms 1202 the remote information pose of the graphical and/or textual information to a local information pose using the local XR headset view pose transform. The processor provides the graphical and/or textual information to the local XR headset 150a/150c for display with the local information pose relative to the local XR headset reference frame.

Some further embodiments are directed to operations that correlate video frames of what is being viewed through the local XR headset 150a/150b and viewed through the remote XR headset 150c to ensure that the associated operators are viewing time synchronized information. In some further embodiments, the processor is operative to correlate in time individual ones of video frames of a local video stream received from the patient tracking camera 200 with individual ones of video frames of a remote video stream received from the remote reference tracking camera, e.g., part of remote XR headset 150c. The processor controls timing when the individual ones of the video frames of the local video stream are provided to the remote XR headset 150c for display based on the correlation, and controls timing when the individual ones of the video frames of the remote video stream are provided to the local XR headset 150a/150b for display based on the correlation.

Operating Room Equipment Visualizations and Control Using XR Headset(s)

Some other embodiments are now described which are directed to camera tracking systems and associated methods and computer program products that enable XR headsets to be used to visualize and control various types of medical equipments.

Positioning and sterility may require a touch free method for controlling medical equipment which may be within reach of an operator or beyond reach. Some embodiments are directed to operations that enable an operator wearing an XR headset to perform hand gestures which are viewed through the XR headset relative to the equipment to be controlled. The hand gestures are tracked by a tracking camera, which may be part of the XR headset, and are recognized by camera tracking system as a command for controlling the proximately located equipment. Information generated by the equipment, such as patient medical measurements and/or operational data, can be displayed through the XR headset with a pose that is anchored proximately located to the associated equipment. In this manner, an operator wearing the XR headset can intuitively view information from various equipment within an OR and may further control operations of the equipment.

With continued reference to FIG. 8, the associated operations can be performed by a tracking camera that provides tracking information to a camera tracking system which is operative to control equipment and provide graphical and/or textual information for display through the XR headset. As explained above, the tracking camera may be part of the XR headset 150*a*/150*b* and/or may be part of an auxiliary camera tracking bar 200.

Movement of medical equipment by the camera tracking system may be performed relative to the patient reference array 116, so as to enable operator gesture based controlled movement of equipment to operator desired poses of the medical equipment relative to the patient.

Figure 13:
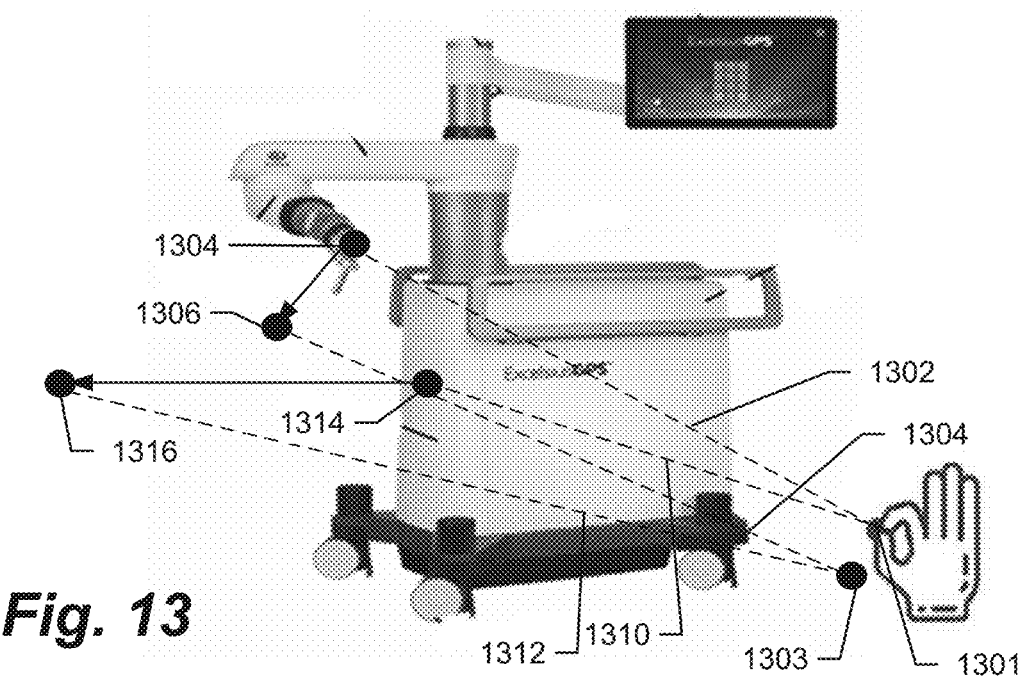
FIG. 13 illustrates an operator controlling movement of an end effector of a surgical robot and/or controlling movement of the surgical robot base using hand gestures which are tracked by a camera tracking system in accordance with some embodiments.

FIG. 13 illustrates an operator controlling movement of an end effector of a surgical robot and/or controlling movement of the surgical robot base using hand gestures which are tracked by a camera tracking system in accordance with some embodiments.

Referring to FIG. 13, in one embodiment the camera tracking system enables an operator to use hand gestures to move an end effector of a surgical robot. The camera tracking system tracks and recognizes an initial gesture by the operator who is pointing a hand-palm or finger from node point 1301 and which the camera tracking system projects along path 1302 to intercept the end effector (e.g., 112 in FIG. 3) at a start end effector location node 1304. The camera tracking systems further tracks and recognizes movement of the operator's fingers, e.g., opening from a pinch gesture, to extend to node point 1303 which the camera tracking system projects along path 1303 to define a target end effector location node 1306. The camera tracking system may display a graphical indication of the planned trajectory via the XR headset along which the end effector is planned to be moved from the starting end effector location node 1304 to the target end effector location node 1306. Responsive to the operator indicating acceptance of the planned trajectory, e.g., by pressing and holding-down a foot pedal or by forming another defined hand gesture, the camera tracking system can control motors of the surgical robot (e.g., 100 in FIG. 3) to move the end effector from the starting end effector location node 1304 to the target end effector location node 1306 along the planned trajectory.

With continued reference to to FIG. 13, in another embodiment the camera tracking system enables an operator to use hand gestures to move location of a surgical robot base, e.g., to position the surgical robot with the desired poses relative to a patient reference frame (e.g., 116 in FIG. 8). The camera tracking system tracks and recognizes an initial gesture by the operator who is pointing a hand-palm or finger from node point 1301 and which the camera tracking system projects along path 1310 to intercept a base (e.g., 106 in FIG. 3) of the surgical robot (e.g., 100 in FIG. 3) at a start base location node 1314. The camera tracking systems further tracks and recognizes movement of the operator's fingers, e.g., opening from a pinch gesture, to extend to node point 1303 which the camera tracking system projects along path 1312 to define a target base location node 1316. The camera tracking system may display a graphical indication of the planned trajectory via the XR headset along which the robot base is planned to be moved from the starting base location node 1314 to the target base location node 1316. Responsive to the operator indicating acceptance of the planned trajectory, e.g., by pressing and holding-down a foot pedal or by forming another defined hand gesture, the camera tracking system can control motors connected to wheels of the robot base to move the robot base from the starting base location node 1314 to the target base location node 1316 along the planned trajectory.

Figure 14:
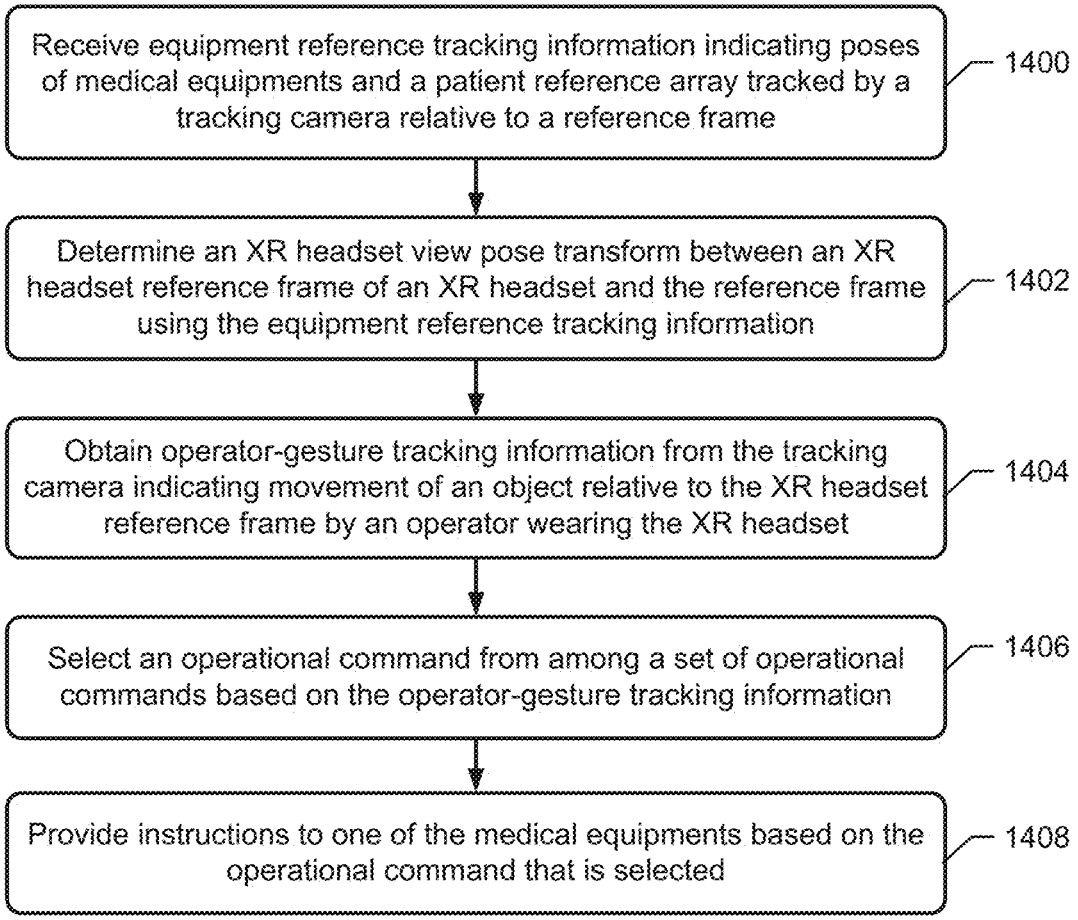
FIG. 14 is a flowchart of operations by a camera tracking system for controlling movement of the end effector and/or the surgical robot base of FIG. 13 using tracked hand gestures, in accordance with some embodiments.

FIG. 14 is a flowchart of operations by a camera tracking system for controlling movement of the end effector (e.g., 112 in FIG. 8) and/or the surgical robot base (e.g., 106 in FIG. 3) using tracked hand gestures, in accordance with some embodiments.

Referring to FIG. 14, the camera tracking system includes at least one processor ("processor") operative to receive 1400 equipment reference tracking information indicating poses of medical equipments and a patient reference array tracked by a tracking camera relative to a reference frame. The processor is operative to determine 1402 an XR headset view pose transform between an XR headset reference frame of an XR headset and the reference frame using the equipment reference tracking information. The processor is operative to obtain 1404 operator-gesture tracking information from the tracking camera indicating movement of an object relative to the XR headset reference frame by an operator wearing the XR headset. The processor is operative to select an operational command from among a set of operational commands based on the operator-gesture tracking information, and to provide instructions to one of the medical equipments based on the operational command that is selected.

As explained above, the tracking camera may be part of the XR headset, and the reference frame may thereby be the same as the XR headset reference frame.

In a further embodiment, the processor is operative to determine a gesture path relative to the XR headset reference frame based on processing the operator-gesture tracking information through the XR headset view pose transform, and to select the operational command from among the set of operational commands based on identifying that the gesture path corresponds to a defined gesture associated with the operational command, wherein the operational commands in the set are associated with different shaped gesture paths.

In a further embodiment, the processor is operative to select the operational command for relocating an end effector connected to a surgical robot arm that is movable under control of a surgical robot system, from among the set of operational commands based on the gesture path corresponding to the defined gesture associated with the operational command for relocating the end effector. The processor is operative to determine a present pose of the end effector based on end effector tracking information indicating pose of the end effector tracked by the tracking camera relative to the reference frame, and to control movement of the end effector by the surgical robot system from the present pose to a target pose relative to the reference frame based on the operational command for relocating the end effector.

In a further embodiment, the processor is operative to determine a planned end effector trajectory path from the present pose to the target pose based on at least a segment of the gesture path, and to control movement of the end effector by the surgical robot system to conform to the planned end effector trajectory path from the present pose to the target pose.

The processor may be operative to determine the planned end effector trajectory path based on tracking movement of fingers and/or a hand of the operator wearing the XR headset relative to the end effector.

In a further embodiment, the processor is operative to select the operational command for relocating medical imaging equipment in a room under control of a computer system, from among the set of operational commands based on the gesture path corresponding to the defined gesture associated with the operational command for relocating the medical imaging equipment. The processor is operative to determine a present location in the room of the medical imaging equipment relative to the reference frame based on the equipment reference tracking information, and to determine a target location in the room for the medical imaging equipment relative to the reference frame based on at least a segment of the gesture path. The processor is operative to control movement of the medical imaging equipment by the computer system from the present location to the target location based on the operational command for relocating the medical imaging equipment.

In a further embodiment, the processor is operative to select the operational command from among the set of operational commands which control at least one of the following:
1) operational settings of a computer assisted surgical navigation system;
2) operational settings of a surgical robot system;
3) operational settings of medical imaging equipment which is operable to obtain medical images of anatomical structure of a patient;
4) operational settings of intraoperative neuromonitoring equipment which is operable to monitor neural structures of a patient;
5) operational settings of the XR headset;
6) operational settings of a computer display;
7) operational settings of a microscope;
8) operational settings of an exoscope;
9) operational setting of a lighting apparatus which is operable to illuminate a patient;
10) operational settings of a powered adjustable surgical bed which is operable to support a patient;
11) operational settings of a microscope;
12) operational settings of anesthesia equipment which is operable to supply anesthesia to a patient;
13) operational settings of a clock and/or timer;
14) operational settings of communication equipment; and
15) operational settings of sound equipment.

In a further embodiment, the processor is operative to obtain first graphical and/or textual information from a first one of the medical equipments, and second graphical and/or textual information from a second one of the medical equipments. The processor displays the first graphical and/or textual information through the XR headset with a pose in the XR headset reference frame defined to be adjacent to the first one of the medical equipments and display the second graphical and/or textual information through the XR headset with another pose in the XR headset reference frame defined to be adjacent to the second one of the medical equipments.

The equipment information may be displayed through the XR headset with a pose that is anchored relative to the associated equipment. In this manner, the operator may look toward a particular equipment to initiate display of the related information with the defined pose relative to the particular equipment. An operator may use one or more hand gestures to control what types of equipment information is displayed, size of the displayed information, and where the displayed information is posed relative to the equipment. An operator may use various defined types of hand gestures to control corresponding settings of the equipment, such as one or more operational threshold levels used by the equipment.

In some further embodiments, the camera tracking system may scan the room to automatically identify medical equipment which is present within the field of view of the tracking cameras. The camera tracking system may process various video streams from one or more XR headsets 150a/150b and/or mounted to an auxiliary tracking bar 200 to identify medical equipment. For example, the camera tracking system may determine a medical equipment type, model number, and/or a unique identifier captured in camera video stream(s) based on identifying a tag or other machine-readable code on the medical equipment and/or based on identifying a tracking array on the medical equipment. Alternatively or additionally, the camera tracking system may identify medical equipment based on matching the shape observed in the camera video stream(s) to a defined geometric shape template for the medical equipment.

The camera tracking system may identify a pose of the medical equipment within the room, and may enable an operator to use a hand gesture to identify a target location for where the medical equipment is to be moved. The camera tracking system may then determine a planned trajectory path for moving the medical equipment from the present pose to the target pose, and may display the plan trajectory path through one of the XR headsets 150a/150b for approval by an operator. The camera tracking system may then control movement of the medical equipment from the present pose to the target pose, such as to position the medical equipment relative to a patient reference array. The human tracking system may also identify in the camera video stream(s) obstacles, such as power lines and/or communication lines extending along the floor, a table, etc., in a path between the present pose and target pose of the medical equipment, and may determine the plan trajectory path to have a shape that avoids such obstacles.

In this manner, the camera tracking system can operate to track world-anchored content in an intuitive manner for viewing by surgeons and other operators during a surgical procedure. A surgical assistant may adjust a surgeon's XR headset parameters from the other side of the bed using hand gestures to interact with a virtual head stabilized interface, and/or may adjust tracking camera operational modes or outputs using hand gestures to interact with a virtual interface displayed adjacent to or overlapping the tracking camera.

Figure 15:
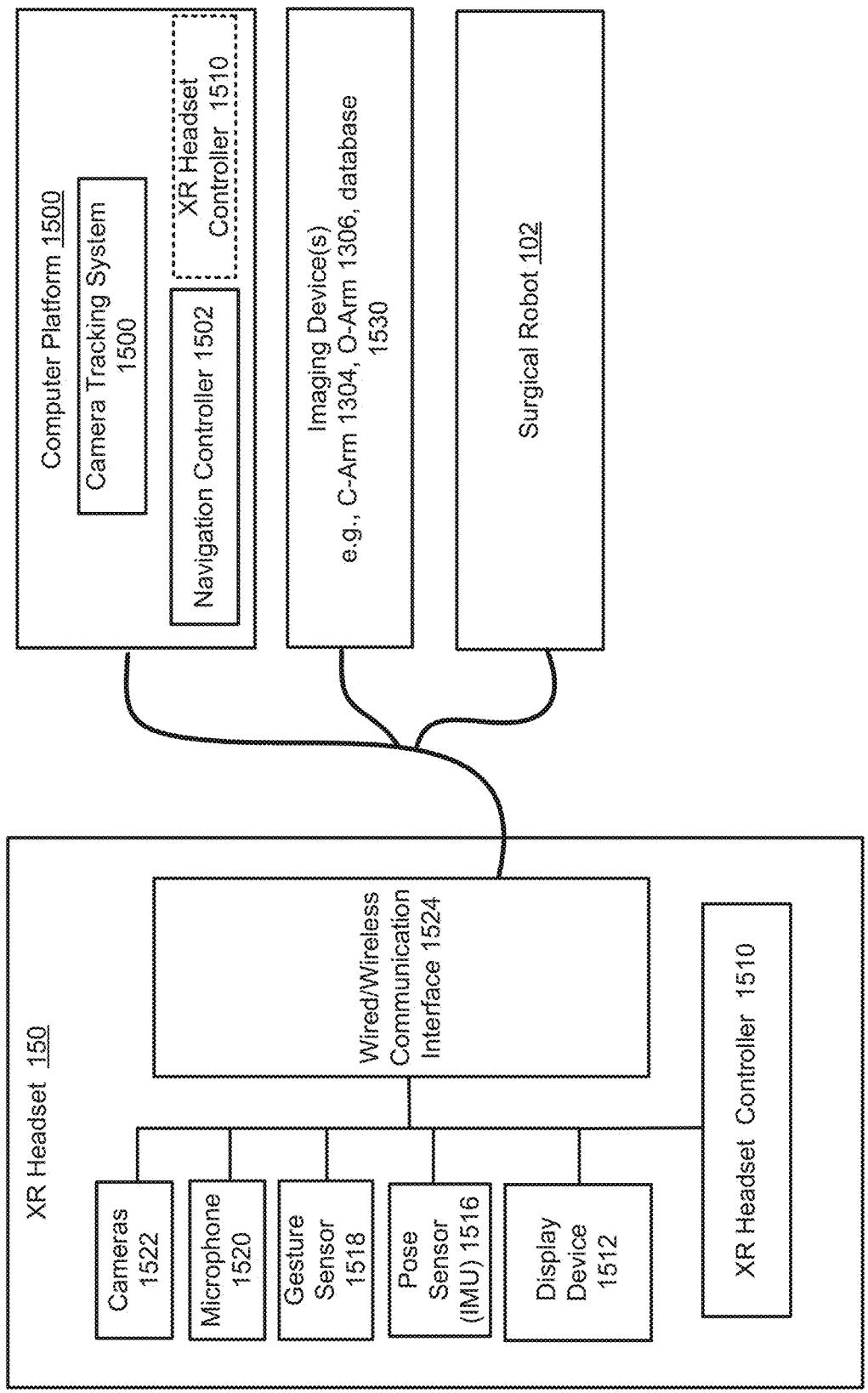
FIG. 15 illustrates a block diagram of a surgical system that includes an XR headset, a computer platform, a camera tracking system component, imaging devices, and a surgical robot which are operative in accordance with some embodiments.

FIG. 15 illustrates a block diagram of a surgical system that includes an XR headset 150, a computer platform 1500, imaging devices, and a surgical robot 102 which are configured to operate in accordance with various embodiments.

The imaging devices may include the C-arm imaging device 1304, the O-arm imaging device 1306, and/or a patient image database 1530. The XR headset 150 provides an improved human interface for performing navigated surgical procedures. The XR headset 150 can be configured to provide functionalities, e.g., via the computer platform 1500, that include without limitation any one or more of: identification of hand gesture based commands, display XR graphical objects on a display device 1512. The display device 1512 may a video projector, flat panel display, etc. The user can view the XR graphical objects as an overlay anchored to particular real-world objects viewed through a see-through display screen. The XR headset 150 may additionally or alternatively be configured to display on the display device 1512 video streams from cameras mounted to one or more XR headsets 150 and other cameras.

Electrical components of the XR headset 150 can include a plurality of cameras 1522, a microphone 1520, a gesture sensor 1518, a pose sensor (e.g., inertial measurement unit (IMU)) 1516, the display device 1512, and a wireless/wired communication interface 1524. The cameras 1522 of the XR headset 150 may be visible light capturing cameras, near infrared capturing cameras, or a combination of both.

The cameras 1522 may be configured to operate as the gesture sensor 1518 by tracking for identification user hand gestures performed within the field of view of the camera(s) 1522. Alternatively the gesture sensor 1518 may be a proximity sensor and/or a touch sensor that senses hand gestures performed proximately to the gesture sensor 1518 and/or senses physical contact, e.g. tapping on the sensor 1518 or an enclosure. The pose sensor 1516, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes a camera tracking system 1500 which may be part of a computer platform 1500 that can also provide functionality of a navigation controller 1502 and/or of the XR headset controller 1510. The surgical system may include the imaging devices and/or a surgical robot 102. The navigation controller 1502 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 1500. The navigation controller 1502 may be further configured to generate steering information based on a target pose for a surgical tool, a pose of the anatomical structure, and a pose of the surgical tool and/or an end effector of the surgical robot 102, where the steering information indicates where the surgical tool and/or the end effector of the surgical robot 102 should be moved to perform the surgical plan.

The electrical components of the XR headset 150 can be operatively connected to the electrical components of the computer platform 1500 through a wired/wireless interface 1524. The electrical components of the XR headset 150 may be operatively connected, e.g., through the computer platform 1500 or directly connected, to various imaging devices, e.g., the C-arm imaging device 1304, the I/O-arm imaging device 1306, the patient image database 1530, and/or to other medical equipment through the wired/wireless interface 1524.

The surgical system further includes at least one XR headset controller 1510 (also referred to as "XR headset controller" for brevity) that may reside in the XR headset 150, the computer platform 1500, and/or in another system component connected via wired cables and/or wireless communication links. Various functionality is provided by software executed by the XR headset controller 1510. The XR headset controller 1510 is configured to receive information from the computer tracking system 1500 and the navigation controller 1502, and to generate an XR image based on the information for display on the display device 1512.

The XR headset controller 1510 can be configured to operationally process signaling from the cameras 1522, the microphone 1520, and/or the pose sensor 1516, and is connected to display XR images on the display device 1512 for user viewing. Thus, the XR headset controller 1510 illustrated as a circuit block within the XR headset 150 is to be understood as being operationally connected to other illustrated components of the XR headset 150 but not necessarily residing within a common housing or being otherwise transportable by the user. For example, the XR headset controller 1510 may reside within the computer platform 1500 which, in turn, may reside within a housing of the surgical robot 102, the tracking cameras 200, etc.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A method by a camera tracking system, the method comprising:
   receiving patient reference tracking information indicating pose of a patient reference array tracked by a patient tracking camera relative to a patient reference frame;
   determining a local extended reality (XR) headset view pose transform between a local XR headset reference frame of a local XR headset and the patient reference frame using the patient reference tracking information;
   receiving remote reference tracking information indicating pose of a remote reference array tracked by a remote reference tracking camera;
   determining a remote XR headset view pose transform between a remote XR headset reference frame of a remote XR headset and the remote reference array using the remote reference tracking information;
   transforming a three-dimensional (3D) computer image from a local pose determined using the local XR headset view pose transform to a remote pose determined using the remote XR headset view pose transform which outputs a transformed 3D computer image; and
   providing the transformed 3D computer image to the remote XR headset for display with the remote pose relative to the remote XR headset reference frame.

2. The method of claim 1, further comprising transforming the 3D computer image from the local pose to the remote pose while the patient tracking camera is remote from the remote reference tracking camera and not positioned to track pose of the remote reference array, and while the remote reference tracking camera is not positioned to track pose of the patient reference array.

3. The method of claim 1, further comprising:
   determining a 4 degree-of-freedom (4 DOF) pose of the remote XR headset based on measured movement along three orthogonal axes of the remote XR headset reference frame and rotation about one of the three orthogonal axes aligned with gravitational direction,
   wherein the transformation of the 3D computer image from the local pose determined using the local XR headset view pose transform to the remote pose determined using the remote XR headset view pose transform comprises processing the 4 DOF pose of the remote XR headset through the remote XR headset view pose transform.

4. The method of claim 1, further comprising:
   obtaining remote operator-gesture tracking information from the remote reference tracking camera indicating movement of an object relative to the remote XR headset reference frame by a remote operator wearing the remote XR headset;

determining a remote gesture path relative to the remote XR headset reference frame based on processing the remote operator-gesture tracking information through the remote XR headset view pose transform; and transforming the remote gesture path to a local gesture path relative to the local XR headset reference frame using the local XR headset view pose transform.

5. The method of claim 4, further comprising:

provide the local gesture path to the local XR headset for display relative to the local XR headset reference frame.

6. The method of claim 4, further comprising:

determining the remote gesture path relative to the remote XR headset reference frame based on tracking movement indicated by the remote operator-gesture tracking information of a hand and/or a stylus which is moved by the remote operator while concurrently viewing the transformed 3D computer image through the remote XR headset relative to the hand and/or stylus being moved.

7. The method of claim 4, further comprising:

selecting an operational command from among a set of operational commands based on the remote gesture path corresponding to defined gesture associated with the operational command, wherein the operational commands in the set are associated with different shaped gesture paths; and providing the operational command to an equipment which is local to the local XR headset.

8. The method of claim 7, further comprising:

selecting the operational command for relocating an end effector connected to a surgical robot arm that is movable under control of a surgical robot system, from among the set of operational commands based on the remote gesture path corresponding to the defined gesture associated with the operational command for relocating the end effector;

determining a present pose of the end effector based on end effector tracking information indicating pose of the end effector tracked by the patient tracking camera relative to the patient reference frame; and controlling movement of the end effector by the surgical robot system from the present pose to a target pose relative to the patient reference frame based on the operational command for relocating the end effector.

9. The method of claim 7, further comprising:

determining a planned end effector trajectory path from the present pose to the target pose based on at least a segment of the remote gesture path; and controlling movement of the end effector by the surgical robot system to conform to the planned end effector trajectory path from the present pose to the target pose.

10. The method of claim 8, wherein:

the transformed 3D computer image comprises a graphical representation of the end effector displayed based on the remote pose relative to the remote XR headset reference frame and comprises a graphical representation of anatomical structure of the patient displayed based on the remote pose relative to the remote XR headset reference frame; and the method further comprising determining a planned end effector trajectory path from a present graphical pose of the graphical representation of the end effector to a target graphical pose of the graphical representation of the end effector based on tracking movement of fingers and/or a hand of the remote operator wearing the remote XR headset relative to the graphical representation of the end effector displayed relative to remote XR headset reference frame, and controlling movement of the end effector by the surgical robot system to conform to the planned end effector trajectory path from the present pose relative to the patient reference frame to the target pose relative to the patient reference frame.

11. The method of claim 7, further comprising:

selecting the operational command from among the set of operational commands which control at least one of the following:

operational settings of a computer assisted surgical navigation system;

operational settings of a surgical robot system;

operational settings of medical imaging equipment which is operable to obtain medical images of anatomical structure of the patient;

operational settings of intraoperative neuromonitoring equipment which is operable to monitor neural structures of the patient;

operational settings of the local XR headset;

operational settings of a computer display which is local to the local XR headset;

operational settings of a microscope which is local to the local XR headset;

operational settings of an exoscope which is local to the local XR headset;

operational setting of a lighting apparatus which is operable to illuminate the patient;

operational settings of a powered adjustable surgical bed which is operable to support the patient;

operational settings of a microscope which is local to the local XR headset;

operational settings of anesthesia equipment which is operable to supply anesthesia to the patient;

operational settings of a clock and/or timer which is local to the local XR headset;

operational settings of communication equipment which is local to the local XR headset; and operational settings of sound equipment which is local to the local XR headset.

12. The method of claim 1, further comprising:

obtaining graphical and/or textual information entered by the remote operator and which is displayed by the remote XR headset with a remote information pose relative to the remote XR headset reference frame using the remote XR headset view pose transform;

transforming the remote information pose of the graphical and/or textual information to a local information pose using the local XR headset view pose transform; and providing the graphical and/or textual information to the local XR headset for display with the local information pose relative to the local XR headset reference frame.

13. The method of claim 1, further comprising:

correlating in time individual ones of video frames of a local video stream received from the patient tracking camera with individual ones of video frames of a remote video stream received from the remote reference tracking camera;

controlling timing when the individual ones of the video frames of the local video stream are provided to the remote XR headset for display based on the correlation; and controlling timing when the individual ones of the video frames of the remote video stream are provided to the local XR headset for display based on the correlation.

* * * * *